US010513705B2

(12) United States Patent
Casella et al.

(10) Patent No.: US 10,513,705 B2
(45) Date of Patent: Dec. 24, 2019

(54) APTAMERS FOR THE TREATMENT OF SICKLE CELL DISEASE

(71) Applicant: THE JOHNS HOPKINS UNIVERSITY, Baltimore, MD (US)

(72) Inventors: James F. Casella, Baltimore, MD (US); Emily Barron-Casella, Baltimore, MD (US); Jeffrey R. Keefer, Baltimore, MD (US); Yolanda Fortenberry, Pikesville, MD (US); Shirley H. Purvis, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 15/923,067

(22) Filed: Mar. 16, 2018

(65) Prior Publication Data

US 2018/0282729 A1   Oct. 4, 2018

Related U.S. Application Data

(62) Division of application No. 14/893,645, filed as application No. PCT/US2014/039519 on May 27, 2014, now abandoned.

(60) Provisional application No. 61/828,142, filed on May 28, 2013.

(51) Int. Cl.
| | |
|---|---|
| *C12N 15/11* | (2006.01) |
| *C12N 15/115* | (2010.01) |
| *G01N 33/53* | (2006.01) |
| *G01N 33/72* | (2006.01) |
| *C07K 14/805* | (2006.01) |

(52) U.S. Cl.
CPC .......... *C12N 15/115* (2013.01); *C07K 14/805* (2013.01); *G01N 33/5308* (2013.01); *G01N 33/721* (2013.01); *C12N 2310/16* (2013.01); *C12N 2320/30* (2013.01)

(58) Field of Classification Search
None
See application file for complete search history.

(56) References Cited

U.S. PATENT DOCUMENTS

| | | |
|---|---|---|
| 3,773,919 A | 11/1973 | Boswell et al. |
| 4,485,045 A | 11/1984 | Regen |
| 4,544,545 A | 10/1985 | Ryan et al. |
| 4,767,628 B1 | 7/1990 | Hutchinson |
| 5,004,602 A | 4/1991 | Hutchinson |
| 5,331,573 A | 7/1994 | Balaji et al. |
| 5,459,127 A | 10/1995 | Felgner et al. |
| 5,500,807 A | 3/1996 | Lavin et al. |
| 5,534,408 A | 7/1996 | Green et al. |
| 5,580,859 A | 12/1996 | Felgner et al. |
| 5,589,466 A | 12/1996 | Felgner et al. |
| 5,693,622 A | 12/1997 | Wolff et al. |
| 5,935,776 A | 8/1999 | Green et al. |
| 2010/0311820 A1 | 12/2010 | Layzer et al. |

FOREIGN PATENT DOCUMENTS

| | | |
|---|---|---|
| EP | 0058481 A1 | 8/1982 |
| EP | 0102324 A2 | 3/1984 |
| EP | 0133988 A2 | 3/1985 |
| WO | 1995018863 A1 | 7/1995 |
| WO | 1995021931 A1 | 8/1995 |
| WO | 1996017823 A1 | 6/1996 |
| WO | 1996025508 A1 | 8/1996 |
| WO | 2012/155134 A2 | 11/2012 |
| WO | 2014/100434 A1 | 6/2014 |

OTHER PUBLICATIONS

Purvis et al., Identification of aptamers that bind to sickle hemoglobin and inhibit its polymerization, Nucleic Acids Therapeutics, vol. 27, pp. 354-364. (Year: 2017).*
Ireson et al. (2006) Mol Cancer Ther 5 (12): 2957-62.
Que-Gewirth et al. (2007) Nature Publishing Group 14, 283-291.
Ulmer et al. (1993) Science 259:1745.
Feigner et al. (1989) Science 337:387.
Langer et al., J. Biomed. Mater. Res. 15:167, 1981.
Langer, Chem. Tech. 12:98, 1982.
Zeng (2000) Comb. Chem. High Throughput Screen. 3:355-62.
Bartlett et al. (1989) Special Pub Royal Chem Soc. 78:182-196.
Kuntz (1992) Science 257:1078-108.
International Search Report and Written Opinion dated Dec. 16, 2014, from related PCT Patent Application No. PCT/US14/39519.
Sundaram P, Kurniawan H, Byrne ME, Wower J., Therapeutic RNA aptamers in clinical trials, Eur J Pharm Sci. Jan. 23, 2013; 48(I-2)259-71. doi:10.1016/j.ejps2012.10.014.
Burnette AD, Nimjee SM, Batchvarova M, Zennadi R, Telen MJ, Nishimura J, Sullenger BA., RNA aptamer therapy for vaso-occlusion in sickle cell disease. Nucleic Acid Ther. Aug. 2011;21(4):275-83. doi: 10.1089/nat.2010.0270.
Rguig, Nucleic Acid Selection against Hemoglobin S to Prevent the Aggregation of Red Blood Cells in Sickle Cell Anemic Patients, N59, Hemoglobin S, Sep. 16, 2011 [online]. [Retrieved on Sep. 2014]. Retrieved from the Internet <URL: https://docs.google.com/document/d/1so6mZ7vjYMlsYqiFvoKlozjp6_6ktJcX73dZ-vkq9xM/edit?hl=en_US&pref=2&pli=1> Especially abstract; p. 3, para 1, Figure 1; p. 3, para 4; p. 4, para 1.
Sidman et al. (1983) Biopolymers 22:547.
Werstuck et al. (1998) Science 282:296.
Chase et al. (1986) Ann. Rev. Biochem. 56:103.
Lippard et al. (1978) Acc. Chem. Res. 11:211.
Halperin et al. (2002) Proteins 47:409-43.
Gohlke & Klebe (2001) Curr Opin Struct Biol. 11:231-5.
Dunbrack et al. (1997) Folding and Design 2:27.
Goodford (1985) J. Med. Chem. 28:849-857.
Kuntz et al. (1982) J. Mol. Biol. 161:269-288.

(Continued)

*Primary Examiner* — Dana H Shin
(74) *Attorney, Agent, or Firm* — John Hopkins Technology Ventures

(57) ABSTRACT

The present invention provides polynucleotide aptamers that selectively bind to and inhibit polymerization of sickle hemoglobin (HbS), pharmaceutical compositions comprising the same, methods of use for diagnostics and treatment of sickle cell disease, methods of use as capture reagents, and methods of rational drug design.

10 Claims, 8 Drawing Sheets

Specification includes a Sequence Listing.

(56) References Cited

OTHER PUBLICATIONS

Brooks et al. (1983) J. Comp. Chem. 4:187-217.
Weiner et al. (1984) J. Am. Chem. Soc. 106:765-784.
Carson (1997) Methods in Enzymology 277:25.
Kraulis (1991) Appl Crystallogr. 24:946.
Navia & Murcko (1992) Current Opinions in Structural Biology 2:202-210.
Verlinde (1994) Structure 2:577-587.
Adachi & Asakura (1979) J. Biol. Chem. 254:7765-7771.
Eaton & Hofrichter (1987) Blood 70:1245-1266.
Knee & Mukerji (2009) Biochemistry 48:9903-9911.
Magdoff-Fairchild et al. (1976) Proc. Nat. Acad. Sci. 73(4):990:994.
Higgins and Sharp (1989) CABIOS. 5:151-153.
Altschul et al. (1990) J. Mol. Biol. 215:403-410.
Eichhorn et al. (1968) J. Am. Chem. Soc. 90:7323.
Dale et al. (1975) Biochemistry 14:2447.
Miranker & Karplus (1991) Proteins: Structure Function and Genetics 11:29-34.
Goodsell & Olson (1990) Proteins: Struct Funct Genet, 8:195-202.
Nishibata & Itai (1991) Tetrahedron 47:8985.
Bohm (1992) J. Comp. Aid Molec. Design 6:61-78.
Cohen et al. (1990) J. Med. Chem. 33:883-894.
Harrington (1998) Comp. Biochem. Physiol. 119B(2):305-309.
Connolly (1983) Science 221:709-713.
Curiel et al. (1992) Hum. Gene Ther. 3: 147-154.
Eppstein et al., Proc. Natl. Acad. Sci. U.S.A. 82:3688-3692, 1985.
Feigner et al. (1988) Proc. Natl. Acad. Sci. USA 84:7413.
Gutsacva DR et al., Blood. Jan. 13, 2011; I 17(2):727-35.
Hwang et al., Proc. Natl. Acad. Sci. U.S.A. 77:4030, 1980.
Hwang et al. (1999) Proc. Natl. Acad. Sci. USA 96:12997-13002.
Wu et al. (1992) J. Biol. Chem. 267:963.
Wu et al. (1988) J. Biol. Chem. 263: 14621.
Wu et al. (1987) J. Biol. Chem. 262:4429.
Zhou J et al., Nov. 2012; Frontiers in Genetics, 3:234.
Machy et al. (1988) Proc. Natl. Acad. Sci. US.A. 85 :8027.

\* cited by examiner

SEQUENCE LISTING

```
<160> NUMBER OF SEQ ID NOS: 65

<210> SEQ ID NO 1
<211> LENGTH: 80
<212> TYPE: RNA
<213> ORGANISM: Artificial Sequence
<220> FEATURE:
<223> OTHER INFORMATION: Synthetic Oligonucleotide Template, wherein n
      is a, c, g, or u
<220> FEATURE:
<221> NAME/KEY: misc_feature
<222> LOCATION: (16)..(55)
<223> OTHER INFORMATION: n is a, c, g, or u

<400> SEQUENCE: 1
gggaggacga ugcggnnnnn nnnnnnnnnn nnnnnnnnnn nnnnnnnnnn nnnnncagac      60
gacucgcuga ggauccgaga                                                  80

<210> SEQ ID NO 2
<211> LENGTH: 80
<212> TYPE: RNA
<213> ORGANISM: Artificial Sequence
<220> FEATURE:
<223> OTHER INFORMATION: Synthetic Aptamer

<400> SEQUENCE: 2
gggaggacga ugcggccgau uagaacuggg cugcgaucgg agauccucua gguuucagac      60
gacucgcuga ggauccgaga                                                  80

<210> SEQ ID NO 3
<211> LENGTH: 80
<212> TYPE: RNA
<213> ORGANISM: Artificial Sequence
<220> FEATURE:
<223> OTHER INFORMATION: Synthetic Aptamer

<400> SEQUENCE: 3
gggaggacga ugcgggccga gggauucggu guagacucug cacaguccug aaaagcagac      60
gacucgcuga ggauccgaga                                                  80

<210> SEQ ID NO 4
<211> LENGTH: 80
<212> TYPE: RNA
<213> ORGANISM: Artificial Sequence
<220> FEATURE:
<223> OTHER INFORMATION: Synthetic Aptamer

<400> SEQUENCE: 4
gggaggacga ugcggccgau uagaacuggg cugaggcguu cugcauuucg gugaucagac      60
gacucgcuga ggauccgaga                                                  80

<210> SEQ ID NO 5
<211> LENGTH: 80
<212> TYPE: RNA
<213> ORGANISM: Artificial Sequence
```

```
<220> FEATURE:
<223> OTHER INFORMATION: Synthetic Aptamer

<400> SEQUENCE: 5
gggaggacga ugcggccgau uagaacuggg cguuccgac ucugaauccg gugaucagac      60
gacucgcuga ggauccgaga                                                80

<210> SEQ ID NO 6
<211> LENGTH: 80
<212> TYPE: RNA
<213> ORGANISM: Artificial Sequence
<220> FEATURE:
<223> OTHER INFORMATION: Synthetic Aptamer

<400> SEQUENCE: 6
gggaggacga ugcgguuggu gaagggaggu cagcauaucu ucccgcggga agcgacggac      60
gacucgcuga ggauccgaga                                                80

<210> SEQ ID NO 7
<211> LENGTH: 80
<212> TYPE: RNA
<213> ORGANISM: Artificial Sequence
<220> FEATURE:
<223> OTHER INFORMATION: Synthetic Aptamer

<400> SEQUENCE: 7
gggaggacga ugcggaucca cggguaaggg ugagggacga caucaaggcg agauucagac      60
gacucgcuga ggauccgaga                                                80

<210> SEQ ID NO 8
<211> LENGTH: 80
<212> TYPE: RNA
<213> ORGANISM: Artificial Sequence
<220> FEATURE:
<223> OTHER INFORMATION: Synthetic Aptamer

<400> SEQUENCE: 8
gggaggacga ugcgguacga uuagaacugg ugccgaacag cgcucguuga agacacagac      60
gacucgcuga ggauccgaga                                                80

<210> SEQ ID NO 9
<211> LENGTH: 80
<212> TYPE: RNA
<213> ORGANISM: Artificial Sequence
<220> FEATURE:
<223> OTHER INFORMATION: Synthetic Aptamer

<400> SEQUENCE: 9
gggaggacga ugcggaggaa guagggguucg uccauugggc gaguggccug uguuacagac      60
gacucgcuga ggauccgaga                                                80

<210> SEQ ID NO 10
<211> LENGTH: 80
<212> TYPE: RNA
<213> ORGANISM: Artificial Sequence
<220> FEATURE:
<223> OTHER INFORMATION: Synthetic Aptamer

<400> SEQUENCE: 10
gggaggacga ugcggcacgg uauaguggag uggguaggca ucgcucgacg agugacagac      60
gacucgcuga ggauccgaga                                                80
```

```
<210> SEQ ID NO 11
<211> LENGTH: 80
<212> TYPE: RNA
<213> ORGANISM: Artificial Sequence
<220> FEATURE:
<223> OTHER INFORMATION: Synthetic Aptamer

<400> SEQUENCE: 11
gggaggacga ugcgggagua gggagguaau cgccacccca acgcggagac agcgacagac    60
gacucgcuga ggauccgaga                                                80

<210> SEQ ID NO 12
<211> LENGTH: 80
<212> TYPE: RNA
<213> ORGANISM: Artificial Sequence
<220> FEATURE:
<223> OTHER INFORMATION: Synthetic Aptamer

<400> SEQUENCE: 12
gggaggacga ugcggucgau aggggggacgg accgcgcugg aaacucaacg uagcacagac    60
gacucgcuga ggauccgaga                                                80

<210> SEQ ID NO 13
<211> LENGTH: 80
<212> TYPE: RNA
<213> ORGANISM: Artificial Sequence
<220> FEATURE:
<223> OTHER INFORMATION: Synthetic Aptamer

<400> SEQUENCE: 13
gggaggacga ugcggcacug augggagugg gaucaguguc gagcgguauc ugcagcagac    60
gacucgcuga ggauccgaga                                                80

<210> SEQ ID NO 14
<211> LENGTH: 80
<212> TYPE: RNA
<213> ORGANISM: Artificial Sequence
<220> FEATURE:
<223> OTHER INFORMATION: Synthetic Aptamer

<400> SEQUENCE: 14
gggaggacga ugcgggagua gggagguaau cgucacccca acgcggagac agcgacagac    60
gacucgcuga ggauccgaga                                                80

<210> SEQ ID NO 15
<211> LENGTH: 79
<212> TYPE: RNA
<213> ORGANISM: Artificial Sequence
<220> FEATURE:
<223> OTHER INFORMATION: Synthetic Aptamer

<400> SEQUENCE: 15
gggaggacga ugcggaagca uacaguuuag ugugcuaggg ugggacucag ugaucagacg    60
acucgcugag gauccgaga                                                 79

<210> SEQ ID NO 16
<211> LENGTH: 80
<212> TYPE: RNA
<213> ORGANISM: Artificial Sequence
<220> FEATURE:
<223> OTHER INFORMATION: Synthetic Aptamer

<400> SEQUENCE: 16
```

```
gggaggacga ugcgguccua cuuuccccaa uuuguaacag cucuccgcac agcagcagac    60
gacucgcuga ggauccgaga                                                80

<210> SEQ ID NO 17
<211> LENGTH: 80
<212> TYPE: RNA
<213> ORGANISM: Artificial Sequence
<220> FEATURE:
<223> OTHER INFORMATION: Synthetic Aptamer

<400> SEQUENCE: 17
gggaggacga ugcggcggug uagggaucgu cagucucgga augaccucac agaagcagac    60
gacucgcuga ggauccgaga                                                80

<210> SEQ ID NO 18
<211> LENGTH: 80
<212> TYPE: RNA
<213> ORGANISM: Artificial Sequence
<220> FEATURE:
<223> OTHER INFORMATION: Synthetic Aptamer

<400> SEQUENCE: 18
gggaggacga ugcggccagc aggaggaugg gugccgcacu cggauauuca cgugucagac    60
gacucgcuga ggauccgaga                                                80

<210> SEQ ID NO 19
<211> LENGTH: 80
<212> TYPE: RNA
<213> ORGANISM: Artificial Sequence
<220> FEATURE:
<223> OTHER INFORMATION: Synthetic Aptamer

<400> SEQUENCE: 19
gggaggacga ugcgggacua agcacaacuc aacuagaacg aaccuauucc aucaucagac    60
gacucgcuga ggauccgaga                                                80

<210> SEQ ID NO 20
<211> LENGTH: 80
<212> TYPE: RNA
<213> ORGANISM: Artificial Sequence
<220> FEATURE:
<223> OTHER INFORMATION: Synthetic Aptamer

<400> SEQUENCE: 20
gggaggacga ugcggaacgg aggagugucc ucucagcuga cagucgugca uacuacagac    60
gacucgcuga ggauccgaga                                                80

<210> SEQ ID NO 21
<211> LENGTH: 80
<212> TYPE: RNA
<213> ORGANISM: Artificial Sequence
<220> FEATURE:
<223> OTHER INFORMATION: Synthetic Aptamer

<400> SEQUENCE: 21
gggaggacga ugcggaacuc gauccaucau cgugacugcg uacgugucaa cuaagcagac    60
gacucgcuga ggauccgaga                                                80

<210> SEQ ID NO 22
<211> LENGTH: 80
<212> TYPE: RNA
```

<213> ORGANISM: Artificial Sequence
<220> FEATURE:
<223> OTHER INFORMATION: Synthetic Aptamer

<400> SEQUENCE: 22
gggaggacga ugcgggacgg ucauagagcc ggccgacauu agagccggga auccacagac    60
gacucgcuga ggauccgaga                                                80

<210> SEQ ID NO 23
<211> LENGTH: 80
<212> TYPE: RNA
<213> ORGANISM: Artificial Sequence
<220> FEATURE:
<223> OTHER INFORMATION: Synthetic Aptamer

<400> SEQUENCE: 23
gggaggacga ugcgguggag aggggaaucg uccugcgcac ucugucuccu gagagcagac    60
gacucgcuga ggauccgaga                                                80

<210> SEQ ID NO 24
<211> LENGTH: 80
<212> TYPE: RNA
<213> ORGANISM: Artificial Sequence
<220> FEATURE:
<223> OTHER INFORMATION: Synthetic Aptamer

<400> SEQUENCE: 24
gggaggacga ugcgguguau ccgccaguau gauuaacauc uauaagcccc uaugucagac    60
gacucgcuga ggauccgaga                                                80

<210> SEQ ID NO 25
<211> LENGTH: 80
<212> TYPE: RNA
<213> ORGANISM: Artificial Sequence
<220> FEATURE:
<223> OTHER INFORMATION: Synthetic Aptamer

<400> SEQUENCE: 25
gggaggacga ugcggcuaac cuuguuaggg ccccauacag caucgaguga cggaucagac    60
gacucgcuga ggauccgaga                                                80

<210> SEQ ID NO 26
<211> LENGTH: 80
<212> TYPE: RNA
<213> ORGANISM: Artificial Sequence
<220> FEATURE:
<223> OTHER INFORMATION: Synthetic Aptamer

<400> SEQUENCE: 26
gggaggacga ugcggugcac aggagguggu acacugcgcu cgauucauca gcgcacagac    60
gacucgcuga ggauccgaga                                                80

<210> SEQ ID NO 27
<211> LENGTH: 80
<212> TYPE: RNA
<213> ORGANISM: Artificial Sequence
<220> FEATURE:
<223> OTHER INFORMATION: Synthetic Aptamer

<400> SEQUENCE: 27
gggaggacga ugcggcaugu gagggaggag guccgcguca uaaacuccag gaccacagac    60
gacucgcuga ggauccgaga                                                80

<210> SEQ ID NO 28
<211> LENGTH: 80
<212> TYPE: RNA
<213> ORGANISM: Artificial Sequence
<220> FEATURE:
<223> OTHER INFORMATION: Synthetic Aptamer

<400> SEQUENCE: 28
gggaggacga ugcggaagca auagcucgcc guacaguugu ccugccguuc guguucagac    60
gacucgcuga ggauccgaga                                                80

<210> SEQ ID NO 29
<211> LENGTH: 80
<212> TYPE: RNA
<213> ORGANISM: Artificial Sequence
<220> FEATURE:
<223> OTHER INFORMATION: Synthetic Aptamer

<400> SEQUENCE: 29
gggaggacga ugcgggagua gggagguaag cagcggacua acgagauucg gugagcagac    60
gacucgcuga ggauccgaga                                                80

<210> SEQ ID NO 30
<211> LENGTH: 80
<212> TYPE: RNA
<213> ORGANISM: Artificial Sequence
<220> FEATURE:
<223> OTHER INFORMATION: Synthetic Aptamer

<400> SEQUENCE: 30
gggaggacga ugcggcgagc aaccggaacu cggcuauuau gaccagccaa cuuaacagac    60
gacucgcuga ggauccgaga                                                80

<210> SEQ ID NO 31
<211> LENGTH: 80
<212> TYPE: RNA
<213> ORGANISM: Artificial Sequence
<220> FEATURE:
<223> OTHER INFORMATION: Synthetic Aptamer

<400> SEQUENCE: 31
gggaggacga ugcggcgagc aaccugaacu cggcuauuag gaccagccaa cuuaacagac    60
gacucgcuga ggauccgaga                                                80

<210> SEQ ID NO 32
<211> LENGTH: 80
<212> TYPE: RNA
<213> ORGANISM: Artificial Sequence
<220> FEATURE:
<223> OTHER INFORMATION: Synthetic Aptamer

<400> SEQUENCE: 32
gggaggacga ugcgggaucg gaaccagcgu gacgaagcgc ggaucaacuc cggugcagac    60
gacucgcuga ggauccgaga                                                80

<210> SEQ ID NO 33
<211> LENGTH: 80
<212> TYPE: RNA
<213> ORGANISM: Artificial Sequence
<220> FEATURE:
<223> OTHER INFORMATION: Synthetic Aptamer

```
<400> SEQUENCE: 33
gggaggacga ugcgggaucg aaccagcgu gacgaagcgc ggaucaacuc cggugcugac    60
gacucgcuga ggauccgaga                                              80

<210> SEQ ID NO 34
<211> LENGTH: 78
<212> TYPE: RNA
<213> ORGANISM: Artificial Sequence
<220> FEATURE:
<223> OTHER INFORMATION: Synthetic Aptamer

<400> SEQUENCE: 34
gggaggacga ugcggccgau uagaacuggg ucgcgcugua cccuagggau cgacagacga   60
cucgcugagg auccgaga                                                78

<210> SEQ ID NO 35
<211> LENGTH: 80
<212> TYPE: RNA
<213> ORGANISM: Artificial Sequence
<220> FEATURE:
<223> OTHER INFORMATION: Synthetic Aptamer

<400> SEQUENCE: 35
gggaggacga ugcggagacc caagcgccac gucuggcaug ugagggagga gguaccagac   60
gacucgcuga ggauccgaga                                              80

<210> SEQ ID NO 36
<211> LENGTH: 80
<212> TYPE: RNA
<213> ORGANISM: Artificial Sequence
<220> FEATURE:
<223> OTHER INFORMATION: Synthetic Aptamer

<400> SEQUENCE: 36
gggaggacga ugcggagagc caagcgccac gucuggcaug ugagggggga gguaccagac   60
gacucgcuga ggauccgaga                                              80

<210> SEQ ID NO 37
<211> LENGTH: 80
<212> TYPE: RNA
<213> ORGANISM: Artificial Sequence
<220> FEATURE:
<223> OTHER INFORMATION: Synthetic Aptamer

<400> SEQUENCE: 37
gggaggacga ugcggaaacu caucgguagc cuuccugcgg ucagucuauu aggaccagac   60
gacucgcuga ggauccgaga                                              80

<210> SEQ ID NO 38
<211> LENGTH: 80
<212> TYPE: RNA
<213> ORGANISM: Artificial Sequence
<220> FEATURE:
<223> OTHER INFORMATION: Synthetic Aptamer

<400> SEQUENCE: 38
gggaggacga ugcggcaauu accucagccu cccuagacac gucgucuauu aggaccagac   60
gacucgcuga ggauccgaga                                              80

<210> SEQ ID NO 39
<211> LENGTH: 80
```

```
<212> TYPE: RNA
<213> ORGANISM: Artificial Sequence
<220> FEATURE:
<223> OTHER INFORMATION: Synthetic Aptamer

<400> SEQUENCE: 39
gggaggacga ugcggcaguc uuccgguaag cacggaggug aggggagcuu agcgucagac      60
gacucgcuga ggauccgaga                                                  80

<210> SEQ ID NO 40
<211> LENGTH: 80
<212> TYPE: RNA
<213> ORGANISM: Artificial Sequence
<220> FEATURE:
<223> OTHER INFORMATION: Synthetic Aptamer

<400> SEQUENCE: 40
gggaggacga ugcggauaug ccaugggucg cucgagugag gucgucuauu aggaccagac      60
gacucgcuga ggauccgaga                                                  80

<210> SEQ ID NO 41
<211> LENGTH: 80
<212> TYPE: RNA
<213> ORGANISM: Artificial Sequence
<220> FEATURE:
<223> OTHER INFORMATION: Synthetic Aptamer

<400> SEQUENCE: 41
gggaggacga ugcggagagc caagcgccac gucuggcaug ugagggagga gguaccagac      60
gacucgcuga ggauccgaga                                                  80

<210> SEQ ID NO 42
<211> LENGTH: 80
<212> TYPE: RNA
<213> ORGANISM: Artificial Sequence
<220> FEATURE:
<223> OTHER INFORMATION: Synthetic Aptamer

<400> SEQUENCE: 42
gggaggacga ugcggauugg cgcuauuagg accagcuccg uccgcaacug gucccgagac      60
gacucgcuga ggauccgaga                                                  80

<210> SEQ ID NO 43
<211> LENGTH: 80
<212> TYPE: RNA
<213> ORGANISM: Artificial Sequence
<220> FEATURE:
<223> OTHER INFORMATION: Synthetic Aptamer

<400> SEQUENCE: 43
gggaggacga ugcgggaaca gacccauggc aaucucgcga cgucuucggc cgcugcagac      60
gacucgcuga ggauccgaga                                                  80

<210> SEQ ID NO 44
<211> LENGTH: 79
<212> TYPE: RNA
<213> ORGANISM: Artificial Sequence
<220> FEATURE:
<223> OTHER INFORMATION: Synthetic Aptamer

<400> SEQUENCE: 44
gggaggacga ugcgguacaa cagguucaua cggcgcguug uuccuuggcu gacgcagacg      60
```
acucgcugag gauccgaga                                                  79

<210> SEQ ID NO 45
<211> LENGTH: 80
<212> TYPE: RNA
<213> ORGANISM: Artificial Sequence
<220> FEATURE:
<223> OTHER INFORMATION: Synthetic Aptamer

<400> SEQUENCE: 45
gggaggacga ugcggcacua uuaggaccag ugccuguugu cucgauaagc uccgccagac     60
gacucgcuga ggauccgaga                                                 80

<210> SEQ ID NO 46
<211> LENGTH: 80
<212> TYPE: RNA
<213> ORGANISM: Artificial Sequence
<220> FEATURE:
<223> OTHER INFORMATION: Synthetic Aptamer

<400> SEQUENCE: 46
gggaggacga ugcggauugg cgcuauuagg accagcuccg uccgcaacug aucccgagac     60
gacucgcuga ggauccgaga                                                 80

<210> SEQ ID NO 47
<211> LENGTH: 80
<212> TYPE: RNA
<213> ORGANISM: Artificial Sequence
<220> FEATURE:
<223> OTHER INFORMATION: Synthetic Aptamer

<400> SEQUENCE: 47
gggaggacga ugcggcuauu aggaccagcc guguagaauu cguagcgaug ugacgcagac     60
gacucgcuga ggauccgaga                                                 80

<210> SEQ ID NO 48
<211> LENGTH: 80
<212> TYPE: RNA
<213> ORGANISM: Artificial Sequence
<220> FEATURE:
<223> OTHER INFORMATION: Synthetic Aptamer

<400> SEQUENCE: 48
gggaggacga ugcgguucgc gcuauuagga ccagugcgaa cguggguaua caugucagac     60
gacucgcuga ggauccgaga                                                 80

<210> SEQ ID NO 49
<211> LENGTH: 80
<212> TYPE: RNA
<213> ORGANISM: Artificial Sequence
<220> FEATURE:
<223> OTHER INFORMATION: Synthetic Aptamer

<400> SEQUENCE: 49
gggaggacga ugcggaacac acgggacgag ccuggcgguu gucgucuauu aggaccagac     60
gacucgcuga ggauccgaga                                                 80

<210> SEQ ID NO 50
<211> LENGTH: 81
<212> TYPE: RNA
<213> ORGANISM: Artificial Sequence
<220> FEATURE:
<223> OTHER INFORMATION: Synthetic Aptamer

<400> SEQUENCE: 50
gggaggacga ugcgggucca ugcuuuaaac ugcaauuucc cguuuacacg ggcugucaga    60
cgacucgcug aggauccgag a    81

<210> SEQ ID NO 51
<211> LENGTH: 80
<212> TYPE: RNA
<213> ORGANISM: Artificial Sequence
<220> FEATURE:
<223> OTHER INFORMATION: Synthetic Aptamer

<400> SEQUENCE: 51
gggaggacga ugcggaccac cgaaucacga ggugcgagac auugguuccc cgccgcagac    60
gacucgcuga ggauccgaga    80

<210> SEQ ID NO 52
<211> LENGTH: 80
<212> TYPE: RNA
<213> ORGANISM: Artificial Sequence
<220> FEATURE:
<223> OTHER INFORMATION: Synthetic Aptamer

<400> SEQUENCE: 52
gggaggacga ugcgggggac aauaguccac gacuacaugu cggugcgucg gaggucagac    60
gacucgcuga ggauccgaga    80

<210> SEQ ID NO 53
<211> LENGTH: 80
<212> TYPE: RNA
<213> ORGANISM: Artificial Sequence
<220> FEATURE:
<223> OTHER INFORMATION: Synthetic Aptamer

<400> SEQUENCE: 53
gggaggacga ugcggcuauu aggaccagcu gccaauguua agucuacccc agcagcagac    60
gacucgcuga ggauccgaga    80

<210> SEQ ID NO 54
<211> LENGTH: 80
<212> TYPE: RNA
<213> ORGANISM: Artificial Sequence
<220> FEATURE:
<223> OTHER INFORMATION: Synthetic Aptamer

<400> SEQUENCE: 54
gggaggacga ugcggcuuac guauggucac ggaggugugg gggaacauac agcagcagac    60
gacucgcuga ggauccgaga    80

<210> SEQ ID NO 55
<211> LENGTH: 80
<212> TYPE: RNA
<213> ORGANISM: Artificial Sequence
<220> FEATURE:
<223> OTHER INFORMATION: Synthetic Aptamer

<400> SEQUENCE: 55
gggaggacga ugcgguuggu gaccuauuca ggcguaggca uauaaacuac gaggccagac    60
gacucgcuga ggauccgaga    80

<210> SEQ ID NO 56

```
<211> LENGTH: 80
<212> TYPE: RNA
<213> ORGANISM: Artificial Sequence
<220> FEATURE:
<223> OTHER INFORMATION: Synthetic Aptamer

<400> SEQUENCE: 56
gggaggacga ugcggcuauu aggaccagcu gccaauguua agucuacccc agcggcagac    60
gacucgcuga ggauccgaga                                                80

<210> SEQ ID NO 57
<211> LENGTH: 80
<212> TYPE: RNA
<213> ORGANISM: Artificial Sequence
<220> FEATURE:
<223> OTHER INFORMATION: Synthetic Aptamer

<400> SEQUENCE: 57
gggaggacga ugcgggcacg acacgccgau uagaacuggg cgaucuuggu cgagccagac    60
gacucgcuga ggauccgaga                                                80

<210> SEQ ID NO 58
<211> LENGTH: 80
<212> TYPE: RNA
<213> ORGANISM: Artificial Sequence
<220> FEATURE:
<223> OTHER INFORMATION: Synthetic Aptamer

<400> SEQUENCE: 58
gggaggacga ugcggcgaua cgaccgcaug aguauaccgu cgugcuuccc ggcugcagac    60
gacucgcuga ggauccgaga                                                80

<210> SEQ ID NO 59
<211> LENGTH: 80
<212> TYPE: RNA
<213> ORGANISM: Artificial Sequence
<220> FEATURE:
<223> OTHER INFORMATION: Synthetic Aptamer

<400> SEQUENCE: 59
gggaggacga ugcggauugg cgcuauuagg accagcuccg uccgcaaccg gucccagac     60 gacucgcuga ggauccgaga                                                80

<210> SEQ ID NO 60
<211> LENGTH: 80
<212> TYPE: RNA
<213> ORGANISM: Artificial Sequence
<220> FEATURE:
<223> OTHER INFORMATION: Synthetic Aptamer

<400> SEQUENCE: 60
gggaggacga ugcggauugg cgcuauuagg accagcuccg uccgcaacug gucccagac     60 gacucgcuga ggauccgaga                                                80

<210> SEQ ID NO 61
<211> LENGTH: 11
<212> TYPE: RNA
<213> ORGANISM: Artificial Sequence
<220> FEATURE:
<223> OTHER INFORMATION: RNA aptamer consensus sequence

<400> SEQUENCE: 61
gaacugggcu g                                                         11
```

```
<210> SEQ ID NO 62
<211> LENGTH: 15
<212> TYPE: RNA
<213> ORGANISM: Artificial Sequence
<220> FEATURE:
<223> OTHER INFORMATION: RNA aptamer consensus sequence

<400> SEQUENCE: 62
caccccaacg cggag                                                   15

<210> SEQ ID NO 63
<211> LENGTH: 12
<212> TYPE: RNA
<213> ORGANISM: Artificial Sequence
<220> FEATURE:
<223> OTHER INFORMATION: RNA aptamer consensus sequence

<400> SEQUENCE: 63
gucuauuagg ac                                                      12

<210> SEQ ID NO 64
<211> LENGTH: 13
<212> TYPE: RNA
<213> ORGANISM: Artificial Sequence
<220> FEATURE:
<223> OTHER INFORMATION: RNA aptamer consensus sequence

<400> SEQUENCE: 64
cuauuaggac cag                                                     13

<210> SEQ ID NO 65
<211> LENGTH: 13
<212> TYPE: RNA
<213> ORGANISM: Artificial Sequence
<220> FEATURE:
<223> OTHER INFORMATION: RNA aptamer consensus sequence

<400> SEQUENCE: 65
cgauuagaac ugg                                                     13
```

APTAMERS FOR THE TREATMENT OF SICKLE CELL DISEASE

CROSS-REFERENCE TO RELATED APPLICATION

This application is a Divisional of U.S. patent application Ser. No. 14/893,645, filed Nov. 24, 2015, which is a 35 U.S.C. § 371 U.S. national entry of International Application PCT/US2014/039519, having an international filing date of May 27, 2014, which claims the benefit of U.S. Provisional Application No. 61/828,142, filed May 28, 2013, the content of each of the aforementioned applications is herein incorporated by reference in their entirety.

INCORPORATION-BY-REFERENCE OF MATERIAL SUBMITTED ELECTRONICALLY

This application contains a sequence listing. It has been submitted electronically via EFS-Web as an ASCII text file entitled "12386_SequenceListing". The sequence listing is 17,509 bytes in size, and was created on Nov. 3, 2015. It is hereby incorporated by reference in its entirety.

BACKGROUND

Sickle cell anemia (SCA), a genetic disorder affecting 1 in 400 African Americans and up to 2% of the population in some areas of Africa, results from the production of an abnormal type of hemoglobin that polymerizes (aggregates) leading to detrimental shape changes in red blood cells (sickling) and significant morbidity and mortality in patients.

Polymerization of sickle hemoglobin (HbS) in the red blood cells of patients with SCA leads to rigid red cells which occlude blood vessels, leading to pain, strokes, organ damage, susceptibility to infection and early death. Present methods known in the art that have been shown to alter the severity of the disorder are complex and labor intensive therapies: 1) bone marrow transplantation; 2) routine blood transfusions; or 3) hydroxyurea, a drug which indirectly (and incompletely) prevents HbS polymerization by inducing the production of another type of hemoglobin (fetal hemoglobin). Accordingly, treatments for SCA are lacking and focus mainly on palliative or symptomatic therapy.

SUMMARY

In some aspects, the presently disclosed subject matter provides polynucleotide aptamers that specifically bind sickle hemoglobin (HbS) in such a way that polymerization of HbS is inhibited without a deleterious effect on hemoglobin's functional capabilities. In certain aspects, the polynucleotide aptamers are RNA aptamers. In other aspects, polynucleotide aptamers inhibit polymerization of HbS. The polynucleotide aptamers may specifically bind oxygenated HbS (oxy-HbS), deoxygenated HbS (deoxy-HbS), or may bind both oxy-HbS and deoxy-HbS. In certain aspects, the polynucleotide aptamers comprise a nucleotide sequence that is at least 70% identical, e.g., at least 75%, 80%, 85%, 90%, 91%, 92%, 93%, 94%, 95%, 96%, 97%, 98%, or 99% identical to any one of SEQ ID NOS:2-60, particularly SEQ ID NOS:2, 4, 31, and 37 or fragments or analogs thereof, more particularly: (a) any one of SEQ ID NOS:2, 4, or 5 wherein the polynucleotide aptamer further comprises a consensus sequence consisting of SEQ ID NO:61; (b) any one of SEQ ID NOS:11 or 14 or wherein the polynucleotide aptamer further comprises a consensus sequence consisting of SEQ ID NO:62; (c) any one of SEQ ID NOS:37, 38, 40, or 49 wherein the polynucleotide further comprises a consensus sequence consisting of SEQ ID NO:63; (d) any one of SEQ ID NOS:31, 37, 38, 40, 42, 45, 46, 47, 48, 49, 53, 56, 59, or 60 wherein the polynucleotide aptamer further comprises a consensus sequence consisting of SEQ ID NO:64; or (e) any one of SEQ ID NOS:2, 4, 5, 8, 34, or 57 wherein the polynucleotide aptamer further comprises a consensus sequence consisting of SEQ ID NO:65. In another aspect, the polynucleotide aptamer of the presently disclosed subject matter comprises a consensus sequence consisting of a nucleotide sequence selected from the group consisting of SEQ ID NOS:61, 62, 63, 64, and 65. Other aspects of the presently disclosed subject matter relate to polynucleotides encoding the polynucleotide aptamers of the invention, vectors comprising the polynucleotide aptamers, and cells comprising the polynucleotide aptamers.

In other aspects, the presently disclosed subject matter provides a method of treating or preventing sickle cell disease in a subject in need thereof, the method comprising administering to the subject a therapeutically effective amount of a polynucleotide aptamer that specifically binds sickle hemoglobin (HbS), where the polynucleotide aptamer inhibits polymerization of HbS. In certain aspects, the polynucleotide aptamers are modified to increase the circulating half-life of the aptamer after administration to a subject. In another aspect, the polynucleotide aptamer is administered in a pharmaceutically acceptable carrier. In other aspects, the sickle cell disease is sickle cell anemia. In yet another aspect, the method of treating or preventing sickle cell disease further comprises contacting the polynucleotide aptamer with an antidote, particularly an oligonucleotide comprising a sequence complementary to at least a portion of the polynucleotide aptamer.

In other aspects, the presently disclosed subject matter provides a method for diagnosing or predicting sickle cell disease in a subject having or at risk of developing sickle cell disease or at risk of passing it on to offspring, the method comprising: (a) obtaining a biological sample from the subject; (b) contacting the biological sample with a polynucleotide aptamer that specifically binds to HbS; and (c) detecting binding of the polynucleotide aptamer with HbS in the biological sample; where detection of binding of the polynucleotide aptamer with HbS in the biological sample is indicative of the subject having or at risk of developing sickle cell disease or at risk of passing it on to offspring. In one aspect, the sickle cell disease is sickle cell anemia. In another aspect, the biological sample comprises whole blood, hemocytes, serum, or plasma. In other aspects, the polynucleotide aptamer is labeled for detection with a fluorescent, luminescent, phosphorescent, radioactive, or colorimetric compound.

In yet other aspects, the presently disclosed subject matter provides a method of purifying hemoglobin from a biological sample, the method comprising: (a) providing a biological sample containing hemoglobin; (b) contacting the biological sample with a polynucleotide aptamer that specifically binds to HbS under conditions effective to bind hemoglobin to the aptamer; and (c) recovering the hemoglobin bound to the aptamer. In one aspect, the step of contacting the biological sample with the polynucleotide aptamer that specifically binds to HbS comprises providing a solid support comprising an aptamer that specifically binds to HbS immobilized onto the solid support through a spacer. In other aspects, the polynucleotide aptamer is modified to enable covalent immobilization or to prevent enzymatic degradation. In another aspect, the biological sample comprises whole blood, hemocytes, serum, or plasma.

In other aspects, the presently disclosed subject matter provides a method of using a three-dimensional structure of a polynucleotide aptamer that specifically binds to HbS and inhibits polymerization of HbS in a drug screening assay comprising: (a) selecting a potential drug by performing rational drug design with the three-dimensional structure of the polynucleotide aptamer that specifically binds to HbS and inhibits polymerization of HbS determined from one or more sets of atomic coordinates; wherein said selecting is performed in conjunction with computer modeling; (b) contacting the potential drug with HbS; (c) detecting the binding of the potential drug with the HbS; and (d) detecting the inhibition of polymerization of HbS by the potential drug; wherein a potential drug is selected as a drug if the potential drug binds to HbS and inhibits polymerization of HbS.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1:
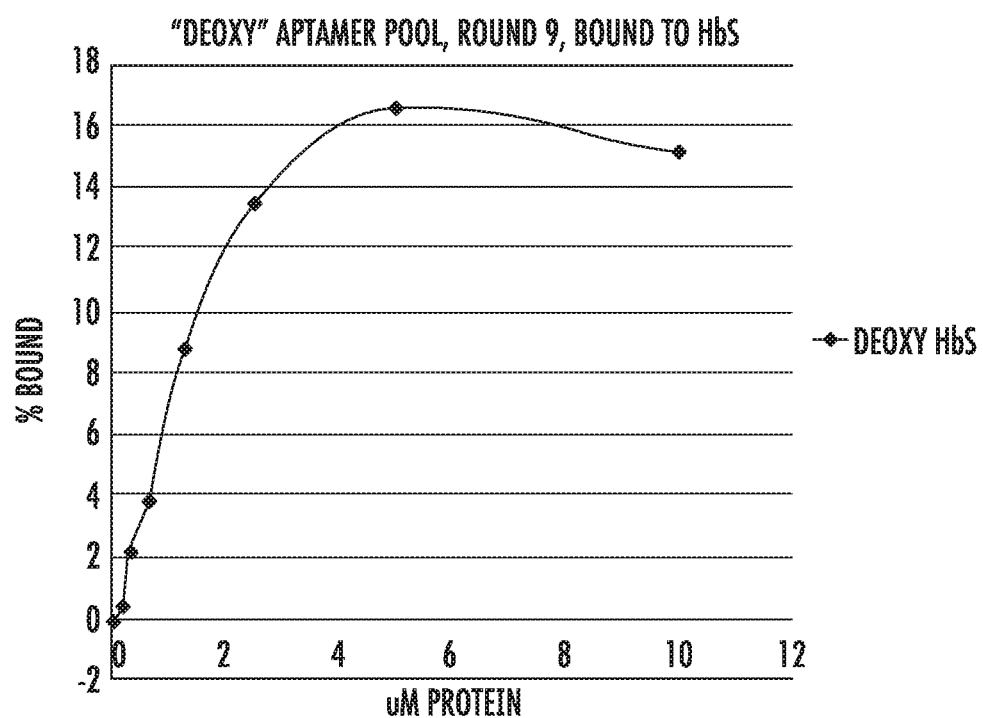
Figure 2:
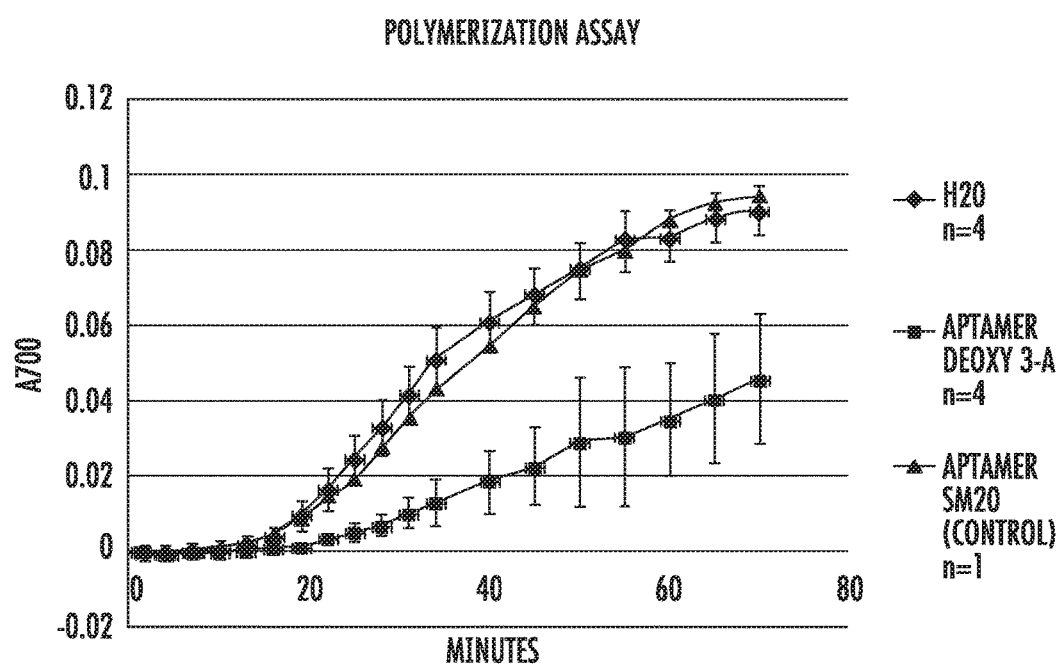
Figure 3:
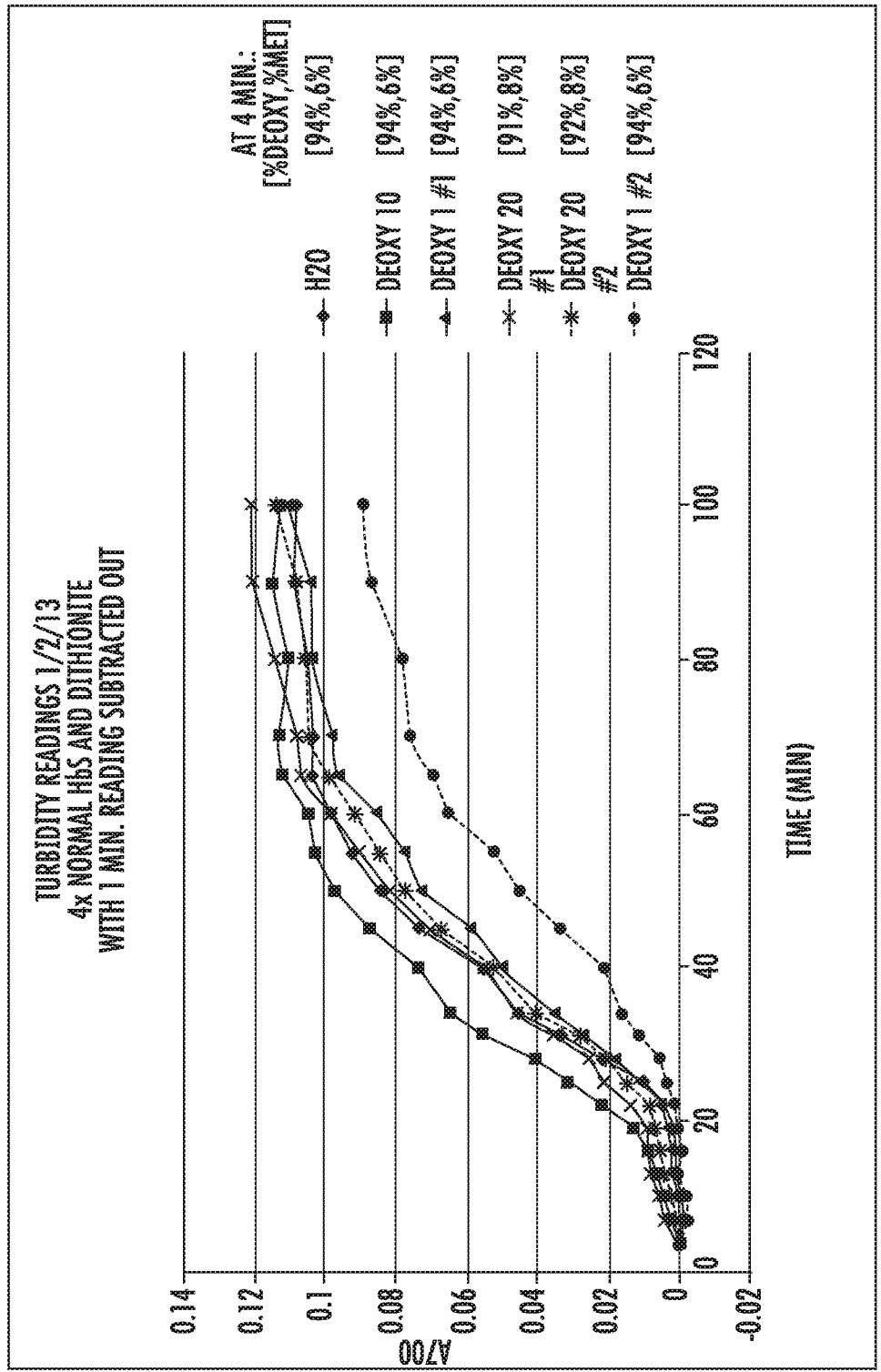
Figure 4:
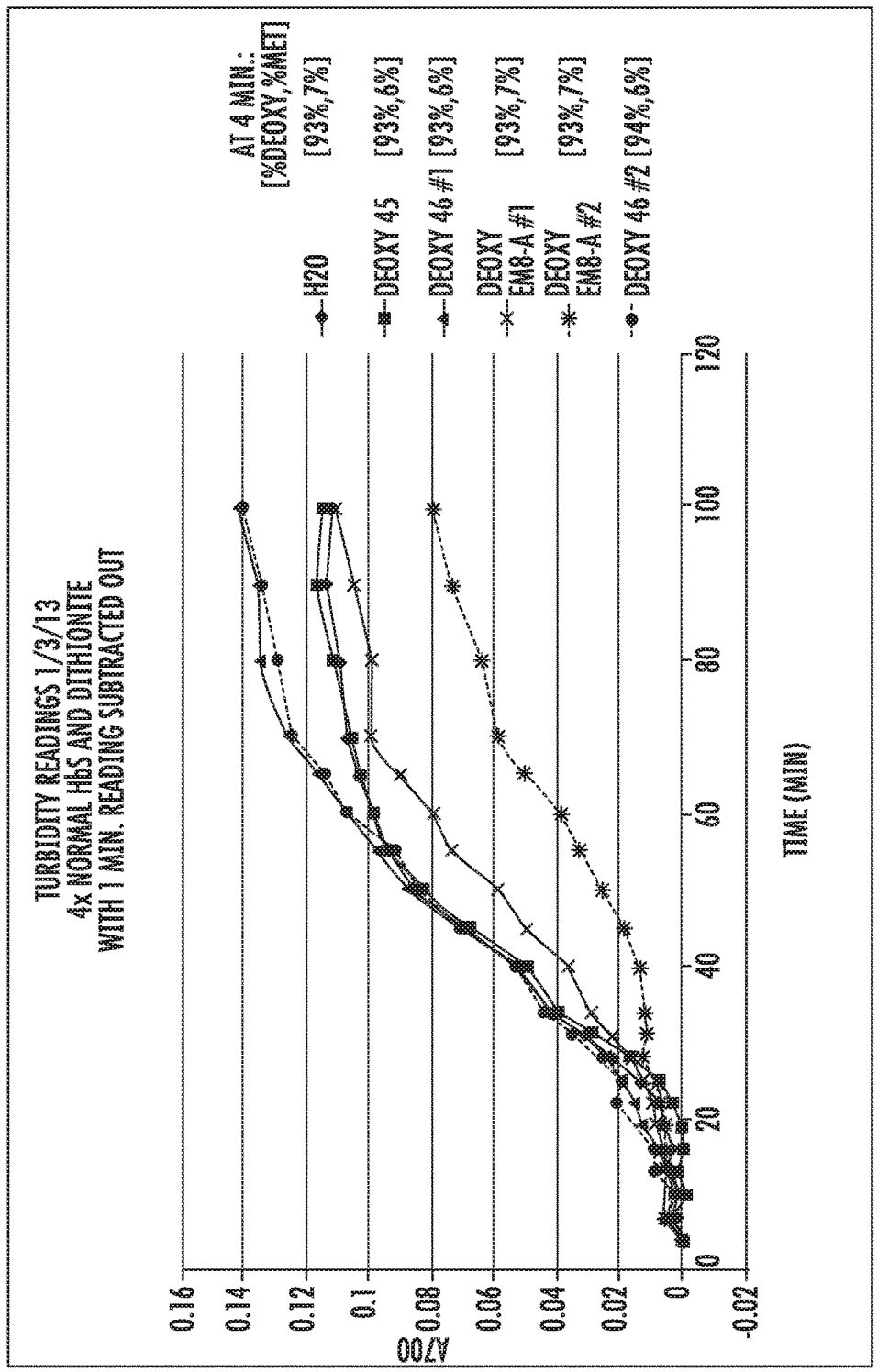
Figure 5:
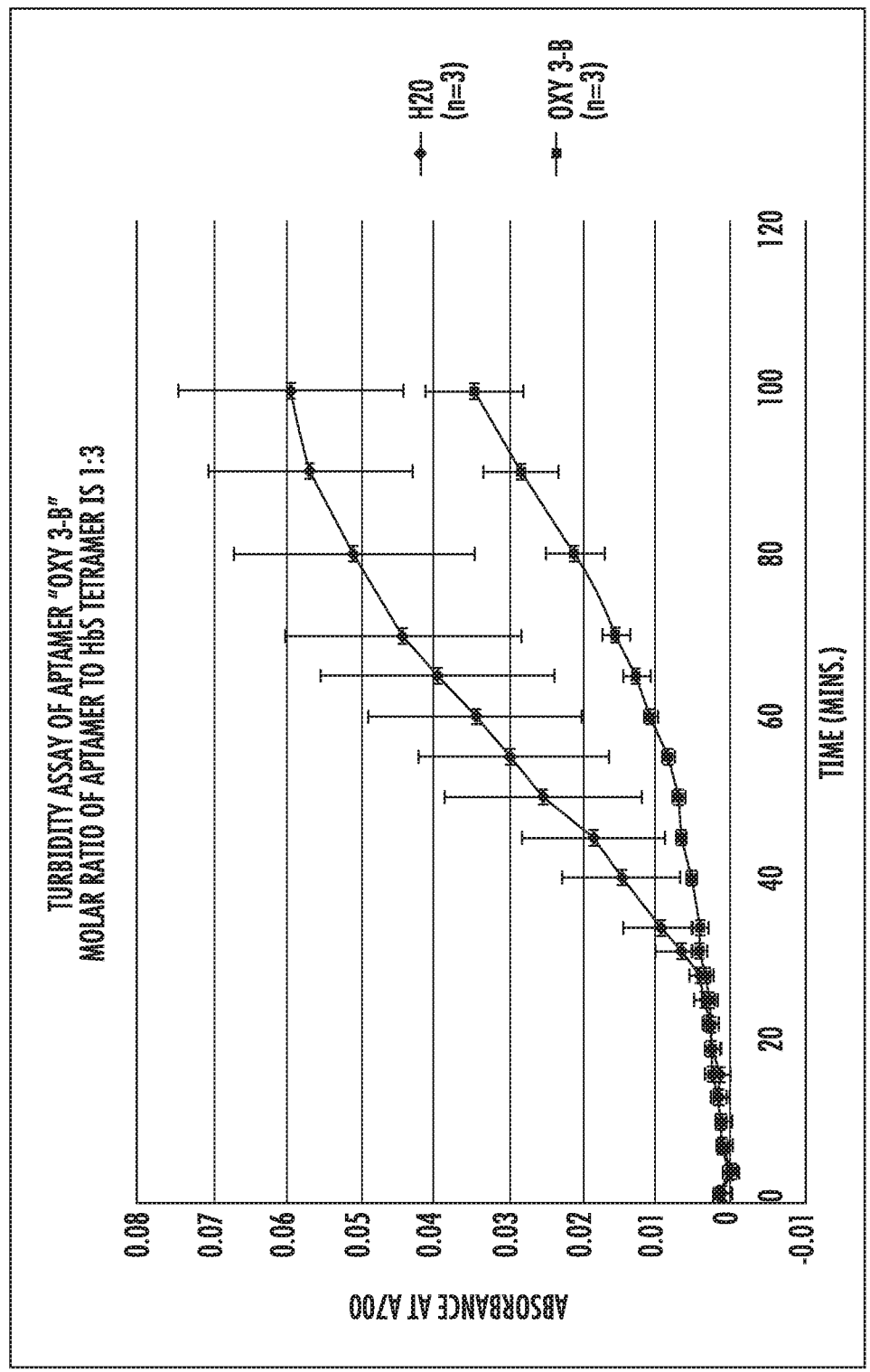
Figure 6A:
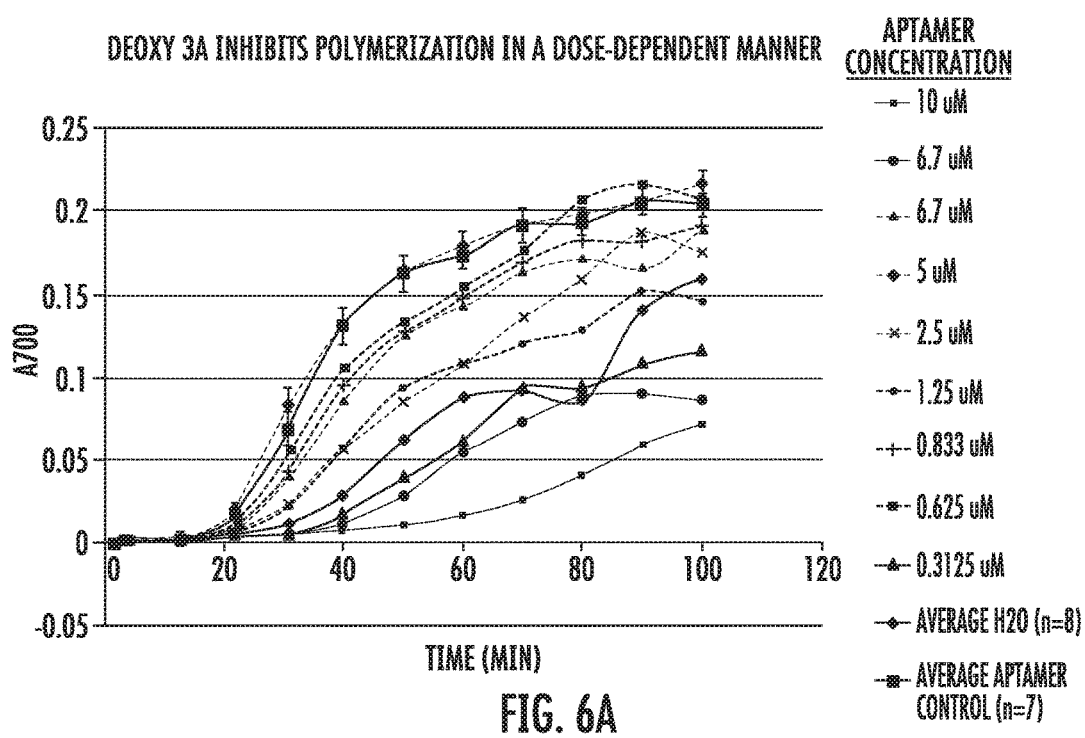
Figure 6B:
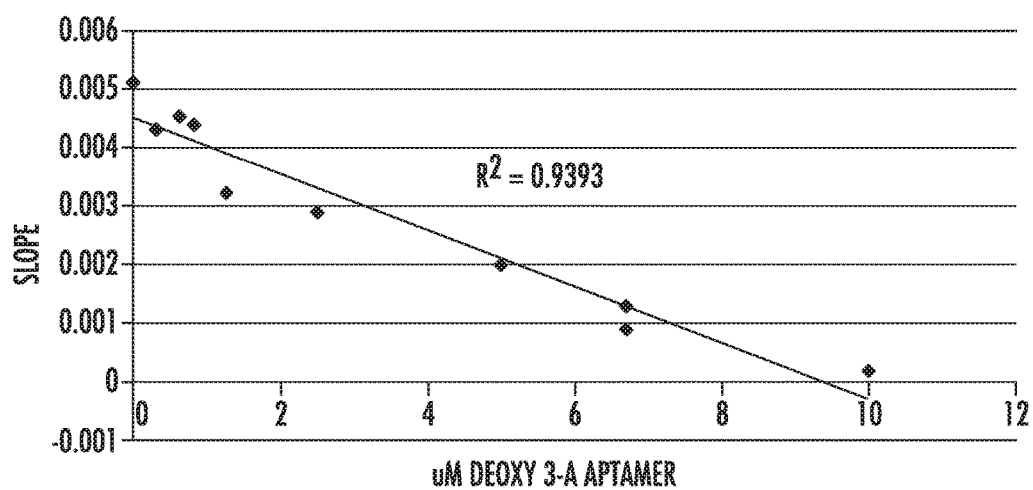
Figure 7:
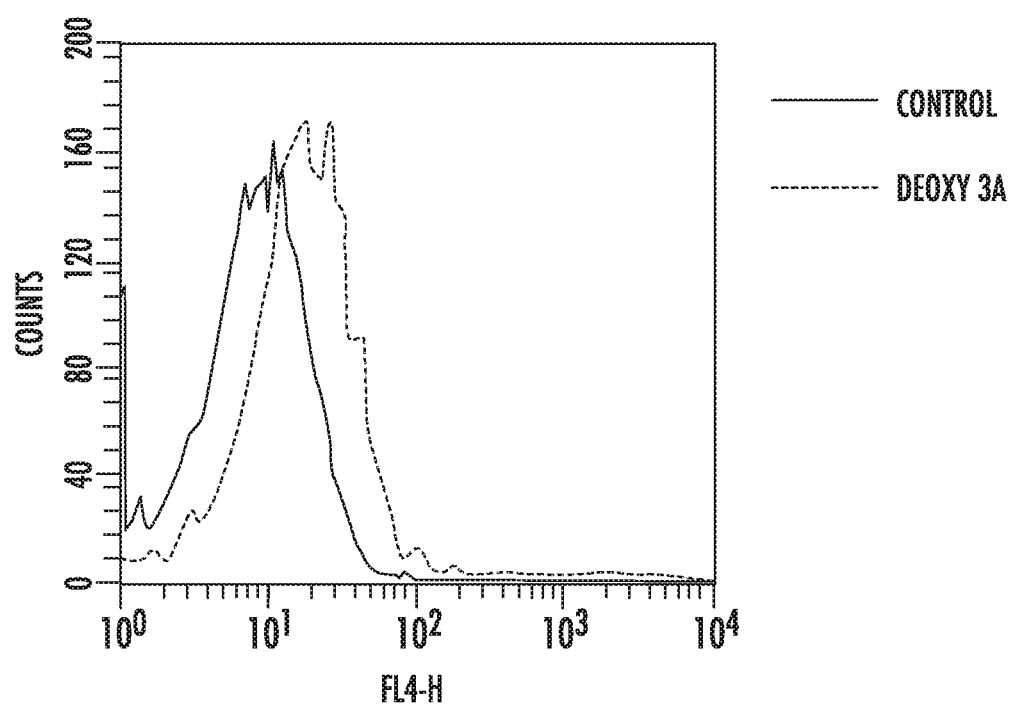
Figure 8:
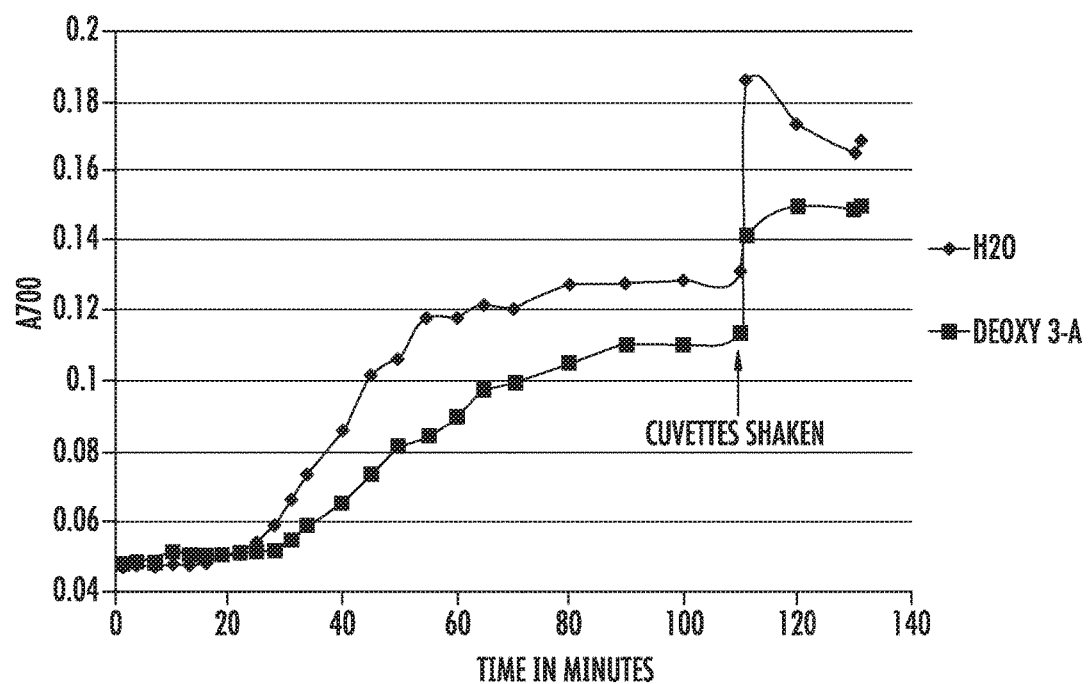

Having thus described the presently disclosed subject matter in general terms, reference will now be made to the accompanying Figures, which are not necessarily drawn to scale, and wherein:

FIG. 1 shows dose-dependent saturable binding of deoxy aptamer to deoxy sickle hemoglobin (HbS);

FIG. 2 shows inhibition of HbS polymerization by deoxy 3-A aptamer (SEQ ID NO:4) in a polymerization assay;

FIG. 3 shows inhibition of HbS polymerization by deoxy 1 aptamer (SEQ ID NO:2) in one of two runs of a polymerization assay;

FIG. 4 shows inhibition of HbS polymerization by deoxy EM8-A aptamer (SEQ ID NO:31) in a polymerization assay;

FIG. 5 shows inhibition of HbS polymerization by oxy 3-B aptamer (SEQ ID NO:37) in a polymerization assay;

FIGS. 6A-6B show the concentration-dependent inhibition of HbS polymerization by deoxy 3-A aptamer: A) polymerization curves as a function of deoxy 3-A aptamer concentration; and B) slope of polymerization curves;

FIG. 7 shows that lipofectin facilitates entry of deoxy 3-A aptamer into sickle red blood cells; and FIG. 8 shows that HbS retains the ability to form new polymer when growing filament ends are provided by mechanical disruption.

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. Hemoglobins and Sickle Cell Disease

Normally, hemoglobin is a tetrameric protein composed of two pairs of two different subunits. Hemoglobin A (hereinafter abbreviated as HbA) has α-chain and β-chain subunits. Binding of glucose to N-terminal amino acid(s) of this/these β-chain results in hemoglobin $A_{1c}$ (hereinafter abbreviated as $HbA_{1c}$). $HbA_{1c}$, if produced via a reversible reaction therebetween, is called labile $HbA_{1c}$ and, if produced via an irreversible reaction involving the labile $HbA_{1c}$, is called stable $HbA_{1c}$.

The separation of hemoglobins present in a hemolyzed sample by means of cation exchange liquid chromatography, if performed over a sufficiently long period of time, generally results in the sequential elution of hemoglobin $A_{1a}$ (hereinafter abbreviated as $HbA_{1a}$) and hemoglobin $A_{1b}$ (hereinafter abbreviated as $HbA_{1b}$), hemoglobin F (hereinafter abbreviated as HbF), labile $HbA_{1c}$, stable $HbA_{1c}$ and hemoglobin $A_0$ (hereinafter abbreviated as $HbA_0$). $HbA_{1a}$, $HbA_{1b}$ and $HbA_{1c}$ each is a glycated HbA. HbF is fetal hemoglobin composed of a and y chains. $HbA_0$ consists of a group of hemoglobin components, includes HbA as its primary component and is retained more strongly to a column than $HbA_{1c}$.

Hemoglobin S or sickle hemoglobin (hereinafter abbreviated as HbS) and hemoglobin C (hereinafter abbreviated as HbC) are known as "abnormal hemoglobins." HbS and HbC result from substitution of glutamic acid located in a sixth position from an N-terminal of the β chain of HbA for valine and lysine, respectively. Hemoglobin $A_2$ (hereinafter abbreviated as $HbA_2$) is composed of a and δ chains and, like HbF, its elevated level is interpreted as evidence of Mediterranean anemia (thalassemia). In the normal determination of hemoglobins by cation exchange liquid chromatography, they are eluted in the sequence of $HbA_0$, $HbA_2$, HbS and HbC.

Sickle-cell disease (SCD), or sickle-cell anemia (or drepanocytosis), is a life-long blood disorder characterized by red blood cells (erythrocytes: RBC) that assume an abnormal, rigid, sickle shape. Sickling decreases flexibility of RBC and results in a risk of various complications. RBC sickling occurs because of a mutation in the hemoglobin gene. SCD is an inherited disorder and SCD is an autosomal recessive disease. Although, some people who inherit one sickle cell gene and one other defective hemoglobin gene may experience a similar sickle-cell disorder. Sickle cell disease includes but is not limited to sickle cell anemia, sickle β-thalassemia, sickle cell-hemoglobin C disease and any other sickle hemoglobinopathy in which HbS interacts with a hemoglobin other than HbS. "Sickle hemoglobinopathy" is an abnormality of hemoglobin which results in sickle cell disease or sickle variants.

II. Polynucleotide Aptamers

A. Aptamers

In some embodiments, the presently disclosed subject matter relates to the generation of aptamers that specifically bind sickle hemoglobin (HbS) in such a way that polymerization of HbS is inhibited without a deleterious effect on hemoglobin's functional capabilities. Aptamers are small single-stranded nucleic acid molecules (~5-25 kDa) that fold into unique structures, allowing them to bind to molecular targets with high specificity and affinity. This specific binding confers the potential for aptamers to be used in a wide variety of diagnostic or therapeutic applications and have emerged as viable alternatives to small-molecule and antibody-based therapy (Que-Gewirth et al. (2007) *Gene Ther.* 14:283; Ireson et al. (2006) *Mol. Cancer Ther.* 5:2957). Like antibodies, aptamers possess binding affinities in the low nanomolar to picomolar range. However, aptamers are advantageous in that they are easily synthesized and stored, can bind very small targets, are non-immunogenic, are heat stable, possess minimal interbatch variability, and can be antidote-controlled. In addition, in contrast to antisense oligonucleotides, RNA aptamers can effectively target extracellular targets, such as HbS. Furthermore, chemical modifications, such as amino or fluoro substitutions at the 2' position of pyrimidines, may reduce degradation by nucleases. The biodistribution and clearance of aptamers can also be altered by chemical addition of moieties such as polyethylene glycol and cholesterol.

An aptamer's small size also maximizes its ability to bind to a specific site on a protein, altering the function of that site, without affecting the functions of other sites on the protein. For example, Fortenberry and colleagues have developed aptamers that bind specifically to plasminogen activator inhibitor-1 (PAI-1), a serine protease inhibitor that has a role in the pathophysiology of several diseases, including cancer and cardiovascular disease. PAI-1 binds to vitronectin, preventing vitronectin's interaction with integrin, thereby resulting in a decrease in cell adhesion and migration. These aptamers bind specifically to PAI-1's vitronectin binding site, affecting PAI-1's interaction with vitronectin, but having no affect on its proteolytic activity.

Specific aptamers are typically selected from very large libraries of more than $10^{14}$ random sequence oligonucleotides in a process called the "systematic evolution of ligands by exponential enrichment" (SELEX). This is an iterative selection process, which begins with a protein or other target of interest being incubated with the oligonucleotide library. A small fraction of the oligonucleotides bind the target and the rest are separated out by a suitable separation technique. The small population that bound the target is then amplified and used in the next round of incubation with the target. This cycle is repeated multiple times, with increasingly stringent incubation and separation conditions at each round in order to enrich for high affinity binders. This process will be referred to herein as "positive selection." However, in certain cases the aptamers that do not bind to the target protein will be amplified, and the binders will be discarded. This process will be referred to herein as "negative selection." Both positive and negative selection may be used, including experiments where the bound aptamers are recovered from the target—positive selection, and experiments where the aptamers that recognized more than one target are removed from the pool (for example, by absorbing pools of molecules that bind both HbA and HbS to HbA, allowing the molecules that specifically bind only to HbS to "flow through"—negative selection).

Accordingly, in one embodiment, the presently disclosed subject matter relates to polynucleotide aptamers that specifically bind to sickle hemoglobin (HbS). In some embodiments, the polynucleotide aptamers inhibit the polymerization of HbS, particularly without a deleterious effect on hemoglobin's functional capabilities. Preventing the polymerization of HbS is essentially a cure for sickle cell anemia, since the complications of the disease arise directly as a result of red blood cell changes brought about by HbS polymerization.

As used herein, "polymerization" includes the process of forming a polymer from many monomeric units of hemoglobin. A polymer may be formed by any chemical bonding interaction between or among molecules, i.e. covalent, ionic, or van der Waals. As used herein, "aggregation" and "polymerization" may be used interchangeably. In particular embodiments, the presently disclosed aptamers inhibit polymerization of HbS. However, it is understood by those of skill in the art that 100% inhibition of polymerization of HbS is not required within the presently disclosed methods. In some embodiments, the presently disclosed methods produce at least about a 10%, 15%, 20%, 25%, 30%, 35%, 40%, 45%, 50%, 55%, 60%, 65%, 70%, 75%, 80%, 85%, 90%, 95%, or even 100% inhibition of polymerization of HbS relative to polymerization of HbS measured in absence of aptamers or modified aptamers described herein that specifically bind HbS and inhibit polymerization of HbS, i.e., a control sample, in an assay.

Thus, one embodiment of the presently disclosed subject matter relates to polynucleotide aptamers that specifically bind to HbS and inhibit polymerization of HbS, particularly without a deleterious effect on hemoglobin's functional capabilities. In another embodiment, the presently disclosed subject matter relates to polynucleotide aptamers that specifically bind to oxygenated HbS (oxy-HbS) or to deoxygenated HbS (deoxy-HbS), or that specifically bind to both oxy-HbS and deoxy-HbS. In one embodiment, the aptamers are DNA or RNA aptamers or hybrid DNA/RNA aptamers. In a particular embodiment, the aptamers are RNA aptamers.

The term "specifically binds," as used herein, refers to a molecule (e.g., an aptamer) that binds to a target (e.g., a protein such as HbS) with at least five-fold greater affinity as compared to any non-targets, e.g., at least 10-, 20-, 50-, or 100-fold greater affinity. The aptamers of the presently disclosed subject matter may bind HbS, including oxy-HbS and/or deoxy-HbS, as well as HbA and other types of hemoglobin, with a $K_d$ of less than about 1000 nM, e.g., less than about 500, 200, 100, 50, or 20 nM.

The sequence of the polynucleotide aptamers of the invention may be selected by any method known in the art. In one embodiment, aptamers are selected by the SELEX process. In another embodiment, aptamers may be selected by starting with the sequences and structural requirements of the aptamers disclosed herein and modifying the sequences to produce other aptamers.

The length of the aptamers of the presently disclosed subject matter is not limited, but typical aptamers have a length of about 10 to about 120 nucleotides, particularly about 80 nucleotides. In certain embodiments, the aptamer may have additional nucleotides attached to the 5'- and/or 3' end. The additional nucleotides may be, e.g., part of primer sequences, restriction endonuclease sequences, or vector sequences useful for producing the aptamer.

The polynucleotide aptamers of the present invention may be comprised of ribonucleotides only (RNA aptamers), deoxyribonucleotides only (DNA aptamers), or a combination of ribonucleotides and deoxyribonucleotides. The nucleotides may be naturally occurring nucleotides (e.g., ATP, TTP, GTP, CTP, UTP) or modified nucleotides. Modified nucleotides refers to nucleotides comprising bases such as, for example, adenine, guanine, cytosine, thymine, and uracil, xanthine, inosine, and queuosine that have been modified by the replacement or addition of one or more atoms or groups. Some examples of types of modifications that can comprise nucleotides that are modified with respect to the base moieties, include but are not limited to, alkylated, halogenated, thiolated, aminated, amidated, or acetylated bases, in various combinations. More specific examples include 5-propynyluridine, 5-propynylcytidine, 6-methyladenine, 6-methylguanine, N,N,-dimethyladenine, 2-propyladenine, 2-propylguanine, 2-aminoadenine, 1-methylinosine, 3-methyluridine, 5-methylcytidine, 5-methyluridine and other nucleotides having a modification at the 5 position, 5-(2-amino)propyl uridine, 5-halocytidine, 5-halouridine, 4-acetylcytidine, 1-methyladenosine, 2-methyladenosine, 3-methylcytidine, 6-methyluridine, 2-methylguanosine, 7-methylguanosine, 2,2-dimethylguanosine, 5-methylaminoethyluridine, 5-methyloxyuridine, deazanucleotides such as 7-deaza-adenosine, 6-azouridine, 6-azocytidine, 6-azothymidine, 5-methyl-2-thiouridine, other thio bases such as 2-thiouridine and 4-thiouridine and 2-thiocytidine, dihydrouridine, pseudouridine, queuosine, archaeosine, naphthyl and substituted naphthyl groups, any O- and N-alkylated purines and pyrimidines such as N6-methyladenosine, 5-methylcarbonylmethyluridine, uridine 5-oxyacetic acid, pyridine-4-one, pyridine-2-one, phenyl and modified phenyl groups such as aminophenol or 2,4,6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxy alkylaminoalkyl nucleotides, and alkylcarbonylalkylated nucleotides. Modified nucleotides also include those nucleotides that are modified with respect to the sugar moiety (e.g., 2'-fluoro or 2'-O-methyl nucleotides), as well as nucleotides having sugars or analogs thereof that are not ribosyl. For example, the sugar moieties may be, or be based on, mannoses, arabinoses, glucopyranoses, galactopyranoses, 4'-thioribose, and other sugars, heterocycles, or carbocycles. The term nucleotide is also meant to include what are known in the art as universal bases. By way of example, universal bases include but are not limited to 3-nitropyrrole, 5-nitroindole, or nebularine. Modified nucleotides include labeled nucleotides such as radioactively, enzymatically, or chromogenically labeled nucleotides).

In one embodiment, the presently disclosed subject matter relates to an RNA aptamer and comprises a nucleotide sequence that is identical to any one of SEQ ID NOS:2-60 as shown in Table 1 (see Example 1). In another embodiment, the RNA aptamer consists of a nucleotide sequence that is identical to any one of SEQ ID NOS:2-60. In a further embodiment, the RNA aptamer comprises a nucleotide sequence that is at least 70% identical, e.g., at least 75%, 80%, 85%, 90%, 91%, 92%, 93%, 94%, 95%, 96%, 97%, 98%, or 99% identical to any one of SEQ ID NOS:2-60. In another embodiment, the aptamer consists of a nucleotide sequence that is at least 70% identical, e.g., at least 75%, 80%, 85%, 90%, 91%, 92%, 93%, 94%, 95%, 96%, 97%, 98%, or 99% identical to any one of SEQ ID NOS:2-60. In yet another embodiment, the aptamer comprises a nucleotide sequence that is identical to a fragment of any one of SEQ ID NOS:2-60 of at least 10 contiguous nucleotides, e.g., at least about 15, 20, 25, 30, or 35 contiguous nucleotides. In another embodiment, the aptamer comprises a nucleotide sequence that is at least 70% identical, e.g., at least 75%, 80%, 85%, 90%, 91%, 92%, 93%, 94%, 95%; 96%, 97%, 98%, or 99% identical to a fragment of any one of SEQ ID NOS: 2-60 of at least contiguous 10 nucleotides, e.g., at least about 15, 20, 25, 30, or 35 contiguous nucleotides. In one embodiment, one or more ribonucleotides in the RNA aptamers described above are substituted by a deoxyribonucleotide. In another embodiment, the fragments and/or analogs of the aptamers of SEQ ID NOS:2-60 have a substantially similar activity as one or more of the aptamers of SEQ ID NOS:2-60. "Substantially similar," as used herein, refers to specific binding to HbS, and in some embodiments also refers to an inhibitory activity on the polymerization of HbS, particularly without a deleterious effect on hemoglobin's functional capabilities, that is at least about 20% of the inhibitory activity of one or more of the aptamers of SEQ ID NOS:2-60.

Changes to the aptamer sequences, such as SEQ ID NOS:2-60, may be made based on structural requirements for binding of the aptamers to HbS, including oxy-HbS and/or deoxy-HbS. The structural requirements may be readily determined by one of skill in the art by analyzing common sequences between the disclosed aptamers and/or by mutagenizing the disclosed aptamers and measuring HbS binding affinity.

When a number of individual, distinct aptamer sequences for a single target molecule have been obtained and sequenced as described herein, the sequences can be examined for "consensus sequences." As used herein, "consensus sequence" refers to a nucleotide sequence or region (which might or might not be made up of contiguous nucleotides) that is found in one or more regions of at least two aptamers, the presence of which can be correlated with aptamer-to-target-binding or with aptamer structure.

A consensus sequence can be as short as three nucleotides long. It also can be made up of one or more noncontiguous sequences with nucleotide sequences or polymers of hundreds of bases long interspersed between the consensus sequences. Consensus sequences can be identified by sequence comparisons between individual aptamer species, which comparisons can be aided by computer programs and other tools for modeling secondary and tertiary structure from sequence information. Generally, the consensus sequence will contain at least about 5 to 20 nucleotides, more commonly from 11 to 15 nucleotides.

In one embodiment, wherein when the RNA aptamer of the presently disclosed subject matter comprises a nucleotide sequence that is at least 70% identical, e.g., at least 75%, 80%, 85%, 90%, 91%, 92%, 93%, 94%, 95%, 96%, 97%, 98%, or 99% identical to any one of SEQ ID NOS:2, 4, or 5 or fragments or analogs thereof, the RNA aptamer further comprises a consensus sequence consisting of GAACUGGGCUG (SEQ ID NO:61).

In another embodiment, wherein when the RNA aptamer of the presently disclosed subject matter comprises a nucleotide sequence that is at least 70% identical, e.g., at least 75%, 80%, 85%, 90%, 91%, 92%, 93%, 94%, 95%, 96%, 97%, 98%, or 99% identical to any one of SEQ ID NOS:11 or 14 or fragments or analogs thereof, the RNA aptamer further comprises a consensus sequence consisting of CAC-CCCAACGCGGAG (SEQ ID NO:62).

In another embodiment, wherein when the RNA aptamer of the presently disclosed subject matter comprises a nucleotide sequence that is at least 70% identical, e.g., at least 75%, 80%, 85%, 90%, 91%, 92%, 93%, 94%, 95%, 96%, 97%, 98%, or 99% identical to any one of SEQ ID NOS:37, 38, 40, or 49, or fragments or analogs thereof, the RNA aptamer further comprises a consensus sequence consisting of GUC-UAUUAGGAC (SEQ ID NO:63).

In another embodiment, wherein when the RNA aptamer of the presently disclosed subject matter comprises a nucleotide sequence that is at least 70% identical, e.g., at least 75%, 80%, 85%, 90%, 91%, 92%, 93%, 94%, 95%, 96%, 97%, 98%, or 99% identical to any one of SEQ ID NOS:31, 37, 38, 40, 42, 45, 46, 47, 48, 49, 53, 56, 59, or 60 or fragments or analogs thereof, the RNA aptamer further comprises a consensus sequence consisting of CUAUUAGGACCAG (SEQ ID NO:64).

In another embodiment, wherein when the RNA aptamer of the presently disclosed subject matter comprises a nucleotide sequence that is at least 70% identical, e.g., at least 75%, 80%, 85%, 90%, 91%, 92%, 93%, 94%, 95%, 96%, 97%, 98%, or 99% identical to any one of SEQ ID NOS:2, 4, 5, 8, 34, or 57, or fragments or analogs thereof, the RNA aptamer further comprises a consensus sequence consisting of CGAUUAGAACUGG (SEQ ID NO:65).

In another embodiment, the RNA aptamer of the presently disclosed subject matter comprises a consensus sequence consisting of a nucleotide sequence selected from the group consisting of SEQ ID NOS:61, 62, 63, 64, and 65.

As used herein, a "nucleic acid" or "polynucleotide" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester anologs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA). A "recombinant DNA molecule" is a DNA molecule that has undergone a molecular biological manipulation.

The term "fragment" refers to a nucleotide sequence of reduced length relative to the reference nucleic acid and comprising, over the common portion, a nucleotide sequence identical to the reference nucleic acid. Such a nucleic acid fragment according to the presently disclosed subject matter may be, where appropriate, included in a larger polynucleotide of which it is a constituent. Such fragments comprise, or alternatively consist of, oligonucleotides ranging in length from at least 6, 8, 9, 10, 12, 15, 18, 20, 21, 22, 23, 24, 25, 30, 39, 40, 42, 45, 48, 50, 51, 54, 57, 60, 63, 66, 70, 75, 78, 80, 90, 100, 105, 120, 135, 150, 200, 300, 500, 720, 900, 1000 or 1500 consecutive nucleotides of a nucleic acid according to the presently disclosed subject matter.

The term "percent identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: Computational Molecular Biology (Lesk, A. M., ed.) Oxford University Press, New York (1988); Biocomputing: Informatics and Genome Projects (Smith, D. W., ed.) Academic Press, New York (1993); Computer Analysis of Sequence Data, Part I (Griffin, A. M., and Griffin, H. G., eds.) Humana Press, New Jersey (1994); Sequence Analysis in Molecular Biology (von Heinje, G., ed.) Academic Press (1987); and Sequence Analysis Primer (Gribskov, M. and Devereux, J., eds.) Stockton Press, New York (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences may be performed using the Clustal method of alignment (Higgins and Sharp (1989) *CABIOS.* 5:151-153) with the default parameters, including default parameters for pair-wise alignments.

The term "sequence analysis software" refers to any computer algorithm or software program that is useful for the analysis of nucleotide or amino acid sequences. "Sequence analysis software" may be commercially available or independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al. (1990) *J. Mol. Biol.* 215:403-410, and DNASTAR (DNASTAR, Inc., Madison, Wis.). Within the context of this application it will be understood that where sequence analysis software is used for analysis, that the results of the analysis will be based on the "default values" of the program referenced, unless otherwise specified. As used herein "default values" will mean any set of values or parameters which originally load with the software when first initialized.

The term "isolated" designates a biological material (nucleic acid or protein) that has been removed from its original environment (the environment in which it is naturally present). For example, a polynucleotide present in the natural state in a plant or an animal is not isolated, however the same polynucleotide separated from the adjacent nucleic acids in which it is naturally present, is considered "isolated". The term "purified" does not require the material to be present in a form exhibiting absolute purity, exclusive of the presence of other compounds.

B. Polynucleotides Encoding Aptamers, Vectors, and Cells

Once an aptamer sequence according to the presently disclosed subject matter is identified, the aptamer may by synthesized by any method known to those of skill in the art. In one embodiment, aptamers may be produced by chemical synthesis of oligonucleotides and/or ligation of shorter oligonucleotides. Accordingly, another embodiment of the present invention relates to polynucleotides encoding the aptamers of the invention. The polynucleotides may be used to express the aptamers, e.g., by in vitro transcription, polymerase chain reaction amplification, or cellular expression. The polynucleotide may be DNA and/or RNA and may be single-stranded or double-stranded. In one embodiment, the polynucleotide is a vector which may be used to express the aptamer. The vector may be, e.g., a plasmid vector or a viral vector and may be suited for use in any type of cell, such as mammalian, insect, plant, fungal, or bacterial cells. The vector may comprise one or more regulatory elements necessary for expressing the aptamers, e.g., a promoter, enhancer, transcription control elements, etc. Another embodiment of the invention relates to a cell comprising a polynucleotide encoding the aptamers of the invention. In another embodiment, the invention relates to a cell comprising the aptamers of the invention. The cell may be any type of cell, e.g., mammalian, insect, plant, fungal, or bacterial cells.

Several methods known in the art may be used to propagate a polynucleotide according to the presently disclosed subject matter. Once a suitable host system and growth conditions are established, recombinant expression vectors can be propagated and prepared in quantity. As described herein, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

A "vector" is any means for the cloning of and/or transfer of a nucleic acid into a host cell. A vector may be a replicon to which another DNA segment may be attached so as to bring about the replication of the attached segment. A "replicon" is any genetic element (e.g., plasmid, phage, cosmid, chromosome, virus) that functions as an autonomous unit of DNA replication in vivo, i.e., capable of replication under its own control. The term "vector" includes both viral and nonviral means for introducing the nucleic acid into a cell in vitro, ex vivo or in vivo. A large number of vectors known in the art may be used to manipulate nucleic acids, incorporate response elements and promoters into genes, etc. Possible vectors include, for example, plasmids or modified viruses including, for example bacteriophages such as lambda derivatives, or plasmids such as pBR322 or pUC plasmid derivatives, or the Bluescript vector. For example, the insertion of the DNA fragments corresponding to response elements and promoters into a suitable vector can be accomplished by ligating the appropriate DNA fragments into a chosen vector that has complementary cohesive termini. Alternatively, the ends of the DNA molecules may be enzymatically modified or any site may be produced by ligating nucleotide sequences (linkers) into the DNA termini. Such vectors may be engineered to contain selectable marker genes that provide for the selection of cells that have incorporated the marker into the cellular genome. Such markers allow identification and/or selection of host cells that incorporate and express the proteins encoded by the marker.

Viral vectors, and particularly retroviral vectors, have been used in a wide variety of gene delivery applications in cells, as well as living animal subjects. Viral vectors that can be used include but are not limited to retrovirus, adeno-associated virus, pox, baculovirus, vaccinia, herpes simplex, Epstein-Barr, adenovirus, geminivirus, and caulimovirus vectors. Non-viral vectors include plasmids, liposomes, electrically charged lipids (cytofectins), DNA-protein complexes, and biopolymers. In addition to a nucleic acid, a vector may also comprise one or more regulatory regions, and/or selectable markers useful in selecting, measuring, and monitoring nucleic acid transfer results (transfer to which tissues, duration of expression, etc.).

Vectors may be introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al. (1992) *J. Biol. Chem.* 267:963; Wu et al. (1988) *J. Biol. Chem.* 263:14621). Aptamers may also be targeted to cells of interest by coupling aptamers to other aptamers that are known to specifically enter cells of interest, which can be screened for, or by attachment to other ligands for red cell receptors that are internalized (e.g., transferrin-transferrin receptors), as described more fully below.

A polynucleotide according to the presently disclosed subject matter can also be introduced in vivo by lipofection. For the past decade, there has been increasing use of liposomes for encapsulation and transfection of nucleic acids in vitro. Synthetic cationic lipids designed to limit the difficulties and dangers encountered with liposome-mediated transfection can be used to prepare liposomes for in vivo transfection of a gene encoding a marker (Feigner et al. (1988) *Proc. Natl. Acad. Sci. USA* 84:7413; Mackey et al. (1988) *Proc. Natl. Acad. Sci. U.S.A.* 85:8027; and Ulmer et al. (1993) *Science* 259:1745). The use of cationic lipids may promote encapsulation of negatively charged nucleic acids, and also promote fusion with negatively charged cell membranes (Feigner et al. (1989) *Science* 337:387). Particularly useful lipid compounds and compositions for transfer of nucleic acids are described in PCT Patent Pubs. WO95/18863 and WO96/17823, and in U.S. Pat. No. 5,459,127. The use of lipofection to introduce exogenous genes into the specific organs in vivo has certain practical advantages. Molecular targeting of liposomes to specific cells represents one area of benefit. It is clear that directing transfection to particular cell types would be particularly preferred in a tissue with cellular heterogeneity, such as pancreas, liver, kidney, and the brain. Lipids may be chemically coupled to other molecules for the purpose of targeting (Mackey et al. (1988) *Proc. Natl. Acad. Sci. U.S.A.* 85:8027). Targeted peptides, e.g., hormones or neurotransmitters, and proteins such as antibodies, or non-peptide molecules could be coupled to liposomes chemically.

Other molecules are also useful for facilitating transfection of a nucleic acid in vivo, such as a cationic oligopeptide (e.g., PCT Patent Pub. WO95/21931), peptides derived from DNA binding proteins (e.g., PCT Patent Pub. WO96/25508), or a cationic polymer (e.g., PCT Patent Pub. WO95/21931).

It is also possible to introduce a vector in vivo as a naked DNA plasmid (see U.S. Pat. Nos. 5,693,622, 5,589,466 and 5,580,859). Receptor-mediated DNA delivery approaches can also be used (Curiel et al. (1992) *Hum. Gene Ther.* 3:147; Wu et al. (1987) *J. Biol. Chem.* 262:4429).

The term "transfection" means the uptake of exogenous or heterologous RNA or DNA by a cell. A cell has been "transfected" by exogenous or heterologous RNA or DNA when such RNA or DNA has been introduced inside the cell. A cell has been "transformed" by exogenous or heterologous RNA or DNA when the transfected RNA or DNA effects a phenotypic change. The transforming RNA or DNA can be integrated (covalently linked) into chromosomal DNA making up the genome of the cell.

The term "promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters." Promoters that cause a gene to be expressed in a specific cell type are commonly referred to as "cell-specific promoters" or "tissue-specific promoters." Promoters that cause a gene to be expressed at a specific stage of development or cell differentiation are commonly referred to as "developmentally-specific promoters" or "cell differentiation-specific promoters." Promoters that are induced and cause a gene to be expressed following exposure or treatment of the cell with an agent, biological molecule, chemical, ligand, light, or the like that induces the promoter are commonly referred to as "inducible promoters" or "regulatable promoters." It is further recognized that since in most cases the exact boundaries of regulatory sequences have not been completely defined, DNA fragments of different lengths may have identical promoter activity.

A "promoter sequence" is a DNA regulatory region capable of binding RNA polymerase in a cell and initiating transcription of a downstream (3' direction) coding sequence. For purposes of defining the presently disclosed subject matter, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease Si), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced (if the coding sequence contains introns) and translated into the protein encoded by the coding sequence.

"Transcriptional and translational control sequences" are DNA regulatory sequences, such as promoters, enhancers, terminators, and the like, that provide for the expression of a coding sequence in a host cell. In eukaryotic cells, polyadenylation signals are control sequences.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

Enhancers that may be used in embodiments of the presently disclosed subject matter include but are not limited to: an SV40 enhancer, a cytomegalovirus (CMV) enhancer, an elongation factor I (EF1) enhancer, yeast enhancers, viral gene enhancers, and the like.

Termination control regions, i.e., terminator or polyadenylation sequences, may also be derived from various genes native to the preferred hosts. In one embodiment of the presently disclosed subject matter, the termination control region may comprise or be derived from a synthetic sequence, synthetic polyadenylation signal, an SV40 late polyadenylation signal, an SV40 polyadenylation signal, a bovine growth hormone (BGH) polyadenylation signal, viral terminator sequences, or the like.

The terms "3' non-coding sequences" or "3' untranslated region (UTR)" refer to DNA sequences located downstream (3') of a coding sequence and may comprise polyadenylation [poly(A)] recognition sequences and other sequences encoding regulatory signals capable of affecting mRNA processing or gene expression. The polyadenylation signal is usually characterized by affecting the addition of polyadenylic acid tracts to the 3' end of the mRNA precursor.

The term "regulatory region" means a nucleic acid sequence that regulates the expression of a second nucleic acid sequence. A regulatory region may include sequences which are naturally responsible for expressing a particular nucleic acid (a homologous region) or may include sequences of a different origin that are responsible for expressing different proteins or even synthetic proteins (a heterologous region). In particular, the sequences can be sequences of prokaryotic, eukaryotic, or viral genes or derived sequences that stimulate or repress transcription of a gene in a specific or non-specific manner and in an inducible or non-inducible manner. Regulatory regions include origins of replication, RNA splice sites, promoters, enhancers, transcriptional termination sequences, and signal sequences which direct the polypeptide into the secretory pathways of the target cell.

C. Modified Aptamers

In one embodiment of the presently disclosed subject matter, the aptamers are modified to increase the circulating half-life of the aptamer after administration to a subject. In one embodiment, the nucleotides of the aptamers are linked by phosphate linkages. In another embodiment, one or more of the internucleotide linkages are modified linkages, e.g., linkages that are resistant to nuclease degradation. The term "modified internucleotide linkage" includes all modified internucleotide linkages known in the art or that come to be known and that, from reading this disclosure, one skilled in the art will conclude is useful in connection with the present invention. Internucleotide linkages may have associated counterions, and the term is meant to include such counterions and any coordination complexes that can form at the internucleotide linkages. Modifications of internucleotide linkages include, without limitation, phosphorothioates, phosphorodithioates, methylphosphonates, 5'-alkylenephosphonates, 5'-methylphosphonate, 3'-alkylene phosphonates, borontrifluoridates, borano phosphate esters and selenophosphates of 3'-5' linkage or 2'-5' linkage, phosphotriesters, thionoalkylphosphotriesters, hydrogen phosphonate linkages, alkyl phosphonates, alkylphosphonothioates, arylphosphonothioates, phosphoroselenoates, phosphorodiselenoates, phosphinates, phosphoramidates, 3'-alkylphosphoramidates, aminoalkylphosphoramidates, thionophosphoramidates, phosphoropiperazidates, phosphoroanilothioates, phosphoroanilidates, ketones, sulfones, sulfonamides, carbonates, carbamates, methylenehydrazos, methylenedimethylhydrazos, formacetals, thioformacetals, oximes, methyleneiminos, methylenemethyliminos, thioamidates, linkages with riboacetyl groups, aminoethyl glycine, silyl or siloxane linkages, alkyl or cycloalkyl linkages with or without heteroatoms of, for example, 1 to 10 carbons that can be saturated or unsaturated and/or substituted and/or contain heteroatoms, linkages with morpholino structures, amides, polyamides wherein the bases can be attached to the aza nitrogens of the backbone directly or indirectly, and combinations of such modified internucleotide linkages. In another embodiment, the aptamers comprise 5'- or 3'-terminal blocking groups to prevent nuclease degradation (e.g., an inverted deoxythymidine or hexylamine).

In a further embodiment, the aptamers are linked to conjugates that increase the circulating half-life, e.g., by decreasing nuclease degradation or renal filtration of the aptamer. Conjugates may include, for example, amino acids, peptides, polypeptides, proteins, antibodies, antigens, toxins, hormones, lipids, nucleotides, nucleosides, sugars, carbohydrates, polymers such as polyethylene glycol and polypropylene glycol, as well as analogs or derivatives of all of these classes of substances. Additional examples of conjugates also include steroids, such as cholesterol, phospholipids, di- and tri-acylglycerols, fatty acids, hydrocarbons that may or may not contain unsaturation or substitutions, enzyme substrates, biotin, digoxigenin, and polysaccharides. Further examples include thioethers such as hexyl-S-tritylthiol, thiocholesterol, acyl chains such as dodecandiol or undecyl groups, phospholipids such as di-hexadecyl-racglycerol, triethylammonium 1,2-di-O-hexadecyl-rac-glycero-3-H-phosphonate, polyamines, polyethylene glycol, adamantane acetic acid, palmityl moieties, octadecylamine moieties, hexylaminocarbonyl-oxycholesterol, farnesyl, geranyl and geranylgeranyl moieties, such as polyethylene glycol, cholesterol, lipids, or fatty acids. Conjugates can also be detectable labels. For example, conjugates can be fluorophores. Conjugates can include fluorophores such as TAMRA, BODIPY, cyanine derivatives such as Cy3 or Cy5 Dabsyl, or any other suitable fluorophore known in the art. A conjugate may be attached to any position on the terminal nucleotide that is convenient and that does not substantially interfere with the desired activity of the aptamer that bears it, for example the 3' or 5' position of a ribosyl sugar. A conjugate substantially interferes with the desired activity of an aptamer if it adversely affects its functionality such that the ability of the aptamer to bind HbS, including oxy-HbS and/or deoxy-HbS, is reduced by greater than 80% in a binding assay.

In a further embodiment, the aptamers as described herein that specifically bind HbS are linked to conjugates to mediate intracellular delivery into a cell of interest. Accordingly another embodiment of the presently disclosed subject matter relates to compositions and methods for intracellular delivery of aptamers as described herein that specifically bind HbS into a cell of interest. "Cell of interest" as used herein refers to red blood cells (RBCs or erythrocytes) and include nucleated or non-nucleated adult and/or fetal red blood cells, but may also refer to erythroblasts, reticulocytes, and/or normoblasts. Such conjugates that mediate intracellular delivery of the aptamers as described herein that specifically bind HbS into a cell of interest include other aptamers that are known to specifically enter cells of interest (referred to herein as "delivery aptamers") or other ligands that bind receptors on a cell of interest and are internalized by the cell (e.g., transferrin and transferrin receptors (CD71) on red blood cells). Such conjugates may further include detectable labels such as fluorophores to facilitate methods of screening cells of interest containing the aptamers as described herein that specifically bind HbS. Where the conjugates are delivery aptamers, the delivery aptamers and the aptamers as described herein that specifically bind HbS may be linked, for example, covalently or functionally through nucleic acid duplex formation. At least one of the linked aptamers may be partly or wholly comprised of 2'-modified RNA or DNA such as 2'F, 2'OH, 2'OMe, 2'allyl, 2'MOE (methoxy-O-methyl) substituted nucleotides, and may contain polyethylene glycol (PEG)-spacers and abasic residues. Covalent linkages for delivery aptamers and other ligands may include, for example, a linking moiety such as a nucleic acid moiety, a PNA moiety, a peptidic moiety, a disulfide bond or a polyethylene glycol (PEG) moiety.

III. Methods of Treatment

A. Methods for Treating Sickle Cell Disease

In one embodiment, the presently disclosed subject matter relates to a method of treating or preventing sickle cell disease in a subject in need thereof, the method comprising administering to the subject a therapeutically effective amount of a polynucleotide aptamer that specifically binds to sickle hemoglobin (HbS) and inhibits polymerization of HbS. In a particular embodiment, the polynucleotide aptamer inhibits polymerization of HbS without a substantial or intolerable deleterious effect on hemoglobin's functional capabilities (e.g., a mild shift in Hb oxygen affinity might be associated with mild to moderate, but tolerable side effects).

As used herein, "sickle cell disease" means that the subject has at least one sickle cell. As used herein, a "sickle cell" includes a cell which is an abnormal, crescent-shaped erythrocyte that contains sickle cell hemoglobin from a subject with sickle cell disease. "Sickling" includes the process whereby a normal-shaped cell becomes crescent-shaped. As described herein, sickle cell disease includes but is not limited to sickle cell anemia, sickle β-thalassemia, sickle cell-hemoglobin C disease and any other sickle hemoglobinopathy in which HbS interacts with a hemoglobin other than HbS. "Sickle hemoglobinopathy" is an abnormality of hemoglobin which results in sickle cell disease or sickle variants.

Any of the aptamers or modified aptamers described herein that specifically bind HbS and inhibit polymerization of HbS, including oxy-HbS and/or deoxy-HbS, may be used within these methods of treating sickle cell disease in a subject in need thereof. In one embodiment, the polynucleotide aptamer that specifically binds to HbS and inhibits polymerization of HbS for use within the methods for treating or preventing sickle cell disease in a subject in need thereof is an RNA aptamer that comprises a nucleotide sequence that is at least 70%, 75%, 80%, 85%, 90%, 91%, 92%, 93%, 94%, 95%, 96%, 97%, 98%, 99%, or 100% identical to any one of SEQ ID NOS:2-60, or a fragment or analog thereof. In a particular embodiment, the polynucleotide aptamer that specifically binds to HbS and inhibits polymerization of HbS for use within the methods for treating or preventing sickle cell disease in a subject in need thereof is an RNA aptamer that comprises a nucleotide sequence that is at least 70%, 75%, 80%, 85%, 90%, 91%, 92%, 93%, 94%, 95%, 96%, 97%, 98%, 99%, or 100% identical to any one of SEQ ID NOS:2, 4, 31, and 37, or, a fragment or analog thereof.

In some embodiments, the presently disclosed methods produce at least about a 10%, 15%, 20%, 25%, 30%, 35%, 40%, 45%, 50%, 55%, 60%, 65%, 70%, 75%, 80%, 85%, 90%, 95%, or even 100% inhibition of polymerization of HbS relative to polymerization of HbS measured in the absence of aptamers or modified aptamers described herein that specifically bind HbS and inhibit polymerization of HbS, i.e., a control sample, in an assay.

In any of the above-described methods, the administering of any of aptamers or modified aptamers described herein that specifically bind HbS and inhibit polymerization of HbS can result in at least about a 10%, 15%, 20%, 25%, 30%, 35%, 40%, 45%, 50%, 55%, 60%, 65%, 70%, 75%, 80%, 85%, 90%, 95%, or even 100% decrease in one or more (e.g., 1, 2, 3, 4, 5, 6, 7, 8, 9, or 10) symptoms of sickle cell disease, compared to a subject that is not administered the aptamers or modified aptamers described herein that specifically bind HbS and inhibit polymerization of HbS.

In any of the above-described methods, the administering of the aptamers or modified aptamers described herein that specifically bind HbS and inhibit polymerization of HbS results in at least about a 10%, 15%, 20%, 25%, 30%, 35%, 40%, 45%, 50%, 55%, 60%, 65%, 70%, 75%, 80%, 85%, 90%, 95%, or even 100% decrease in the likelihood of developing sickle cell disease in a subject, compared to a control population of subjects that are not administered the aptamers or modified aptamers described herein that specifically bind HbS and inhibit polymerization of HbS.

As used herein, the term "inhibit" or "inhibits" means to decrease, suppress, attenuate, diminish, arrest, or stabilize the development or progression of a disease, disorder, or condition, the activity of a biological pathway, or a biological activity such as polymerization of HbS, e.g., by at least 10%, 20%, 30%, 40%, 50%, 60%, 70%, 80%, 90%, 95%, 98%, 99%, or even 100% compared to an untreated control subject, cell, biological pathway, or biological activity. By the term "decrease" is meant to inhibit, suppress, attenuate, diminish, arrest, or stabilize a symptom of a sickle cell disease, disorder, or condition. Sickle cell disease associated symptoms include, but are not limited to, erythrocyte (RBC) sickling, oxygen release, increased HbS polymerization, hemolysis, tissue congestion and organ damage or dysfunction. It will be appreciated that, although not precluded, treating a disease, disorder or condition does not require that the disease, disorder, condition or symptoms associated therewith be completely eliminated.

The method described above for treating or preventing sickle cell disease in a subject in need thereof may be carried out using a single aptamer targeted to HbS, or may be carried out using two or more different aptamers targeted to HbS, e.g., three, four, five, or six different aptamers.

For use within the methods for treating or preventing sickle cell disease in a subject in need thereof, the aptamers described herein that specifically bind to HbS and inhibit polymerization of HbS may optionally be administered in conjunction with other compounds (e.g., therapeutic agents) or treatments (e.g., hydroxyurea or blood transfusions) useful in treating sickle cell disease. The other compounds or treatments may optionally be administered concurrently. As used herein, the word "concurrently" means sufficiently close in time to produce a combined effect (that is, concurrently may be simultaneously, or it may be two or more events occurring within a short time period before or after each other). The other compounds may be administered separately from the aptamers as disclosed herein, or may be combined together with the aptamers as disclosed herein in a single composition.

As used herein, the terms "treat," "treating," "treatment," and the like, are meant to decrease, suppress, attenuate, diminish, arrest, the underlying cause of a disease, disorder, or condition, or to stabilize the development or progression of a disease, disorder, condition, and/or symptoms associated therewith. The terms "treat," "treating," "treatment," and the like, as used herein can refer to curative therapy, prophylactic therapy, and preventative therapy. Accordingly, as used herein, "treating" means either slowing, stopping or reversing the progression of the sickling of a cell, including reversing the progression to the point of eliminating the presence of sickled cells and/or reducing or eliminating the amount of polymerization of hemoglobin, or the amelioration of symptoms associated with sickle cell disease. Sickle cell disease associated symptoms include, but are not limited to, erythrocyte (RBC) sickling, oxygen release, increased HbS polymerization, hemolysis, tissue congestion and organ damage or dysfunction. The treatment, administration, or therapy can be consecutive or intermittent. Consecutive treatment, administration, or therapy refers to treatment on at least a daily basis without interruption in treatment by one or more days. Intermittent treatment or administration, or treatment or administration in an intermittent fashion, refers to treatment that is not consecutive, but rather cyclic in nature. Treatment according to the presently disclosed methods can result in complete relief or cure from a disease, disorder, or condition, or partial amelioration of one or more symptoms of the disease, disease, or condition, and can be temporary or permanent. The term "treatment" also is intended to encompass prophylaxis, therapy and cure.

As used herein, the terms "prevent," "preventing," "prevention," "prophylactic treatment" and the like refer to reducing the probability of developing a disease, disorder, or condition in a subject, who does not have, but is at risk of or susceptible to developing a disease, disorder, or condition. Thus, in some embodiments, an agent can be administered prophylactically to prevent the onset of a disease, disorder, or condition, or to prevent the recurrence of a disease, disorder, or condition.

The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing disease, disorder, condition or the prophylactic treatment for preventing the onset of a disease, disorder, or condition or an animal subject for medical, veterinary purposes, or developmental purposes. Suitable animal subjects include mammals including, but not limited to, primates, e.g., humans, monkeys, apes, gibbons, chimpanzees, orangutans, macaques and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, guinea pigs, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a disease, disorder, or condition. Thus, the terms "subject" and "patient" are used interchangeably herein. Subjects also include animal disease models (e.g., rats or mice used in experiments, and the like).

B. Pharmaceutical Compositions

The presently disclosed pharmaceutical compositions and formulations include pharmaceutical compositions of aptamers that specifically bind to HbS and inhibit polymerization of HbS as disclosed herein, alone or in combination with one or more additional therapeutic agents, in admixture with a physiologically compatible carrier, which can be administered to a subject, for example, a human subject, for therapeutic or prophylactic treatment. As used herein, "physiologically compatible carrier" refers to a physiologically acceptable diluent including, but not limited to water, phosphate buffered saline, or saline, and, in some embodiments, can include an adjuvant. Acceptable carriers, excipients, or stabilizers are nontoxic to recipients at the dosages and concentrations employed, and can include buffers such as phosphate, citrate, and other organic acids; antioxidants including ascorbic acid, BHA, and BHT; low molecular weight (less than about 10 residues) polypeptides; proteins, such as serum albumin, gelatin or immunoglobulins; hydrophilic polymers, such as polyvinylpyrrolidone, amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counter-ions such as sodium; and/or nonionic surfactants such as Tween, Pluronics, or PEG. Adjuvants suitable for use with the presently disclosed compositions include adjuvants known in the art including, but not limited to, incomplete Freund's adjuvant, aluminum phosphate, aluminum hydroxide, and alum.

Compositions to be used for in vivo administration must be sterile, which can be achieved by filtration through sterile filtration membranes, prior to or following lyophilization and reconstitution. Therapeutic compositions may be placed into a container having a sterile access port, for example, an intravenous solution bag or vial having a stopper pierceable by a hypodermic injection needle.

In certain embodiments, the presently disclosed subject matter also includes combination therapies. Additional therapeutic agents, which are normally administered to treat or prevent sickle cell disease, may be administered in combination with aptamers that specifically bind to HbS and inhibit polymerization of HbS as disclosed herein. These additional agents may be administered separately, as part of a multiple dosage regimen, from the composition comprising aptamers that specifically bind to HbS and inhibit polymerization of HbS as disclosed herein. Alternatively, these agents may be part of a single dosage form, mixed together with the aptamers that specifically bind to HbS and inhibit polymerization of HbS as disclosed herein, in a single composition.

By "in combination with" is meant the administration of a aptamers that specifically bind to HbS and inhibit polymerization of HbS as disclosed herein, with one or more therapeutic agents either simultaneously, sequentially, or a combination thereof. Therefore, a subject administered a combination of aptamers that specifically bind to HbS and inhibit polymerization of HbS as disclosed herein, can receive an aptamer that specifically binds to HbS and inhibits polymerization of HbS as disclosed herein, and one or more therapeutic agents at the same time (i.e., simultaneously) or at different times (i.e., sequentially, in either order, on the same day or on different days), so long as the effect of the combination of both agents is achieved in the subject. When administered sequentially, the agents can be administered within 1, 5, 10, 30, 60, 120, 180, 240 minutes or longer of one another. In other embodiments, agents administered sequentially, can be administered within 1, 5, 10, 15, 20 or more days of one another. Where the aptamer that specifically binds to HbS and inhibits polymerization of HbS as disclosed herein, and one or more therapeutic agents are administered simultaneously, they can be administered to the subject as separate pharmaceutical compositions, each comprising either an aptamer that specifically binds to HbS and inhibits polymerization of HbS as disclosed herein, or one or more therapeutic agents, or be administered to a subject as a single pharmaceutical composition comprising both agents.

When administered in combination, the effective concentration of each of the agents to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times. In such combination therapies, the therapeutic effect of the first administered agent is not diminished by the sequential, simultaneous or separate administration of the subsequent agent(s).

C. Dosage and Mode of Administration

The presently disclosed pharmaceutical compositions can be administered using a variety of methods known in the art depending on the subject and the particular disease, disorder, or condition being treated. The administering can be carried out by, for example, intravenous infusion; injection by intravenous, intraperitoneal, intracerebral, intramuscular, intraocular, intraarterial or intralesional routes; or topical or ocular application.

More particularly, as described herein, the presently disclosed aptamers that specifically bind to HbS and inhibit polymerization of HbS can be administered to a subject for therapy by any suitable route of administration, including orally, nasally, transmucosally, ocularly, rectally, intravaginally, parenterally, including intramuscular, subcutaneous, intramedullary injections, as well as intrathecal, direct intraventricular, intravenous, intra-articular, intra-sternal, intrasynovial, intra-hepatic, intralesional, intracranial, intraperitoneal, intranasal, or intraocular injections, intracisternally, topically, as by powders, ointments or drops (including eyedrops), including buccally and sublingually, transdermally, through an inhalation spray, or other modes of delivery known in the art.

The phrases "systemic administration," "administered systemically," "peripheral administration" and "administered peripherally" as used herein mean the administration of an aptamer that specifically binds to HbS and inhibits polymerization of HbS, a compound, drug or other material other than directly into the central nervous system, such that it enters the patient's system and, thus, is subject to metabolism and other like processes, for example, subcutaneous administration.

The phrases "parenteral administration" and "administered parenterally" as used herein mean modes of administration other than enteral and topical administration, usually by injection, and includes, without limitation, intravenous, intramuscular, intarterial, intrathecal, intracapsular, intraorbital, intraocular, intracardiac, intradermal, intraperitoneal, transtracheal, subcutaneous, subcuticular, intraarticular, subcapsular, subarachnoid, intraspinal and intrasternal injection and infusion.

The presently disclosed pharmaceutical compositions can be manufactured in a manner known in the art, e.g. by means of conventional mixing, dissolving, granulating, dragee-making, levitating, emulsifying, encapsulating, entrapping or lyophilizing processes.

More particularly, pharmaceutical compositions for oral use can be obtained through combination of an aptamer that specifically binds to HbS and inhibits polymerization of HbS with a solid excipient, optionally grinding a resulting mixture, and processing the mixture of granules, after adding suitable auxiliaries, if desired, to obtain tablets or dragee cores. Suitable excipients include, but are not limited to, carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethyl cellulose; and gums including arabic and tragacanth; and proteins, such as gelatin and collagen; and polyvinylpyrrolidone (PVP:povidone). If desired, disintegrating or solubilizing agents, such as cross-linked polyvinyl pyrrolidone, agar, alginic acid, or a salt thereof, such as sodium alginate, also can be added to the compositions.

Dragee cores are provided with suitable coatings, such as concentrated sugar solutions, which also can contain gum arabic, talc, polyvinylpyrrolidone, carbopol gel, polyethylene glycol (PEG), and/or titanium dioxide, lacquer solutions, and suitable organic solvents or solvent mixtures. Dyestuffs or pigments can be added to the tablets or dragee coatings for product identification or to characterize the quantity of an aptamer that specifically binds to HbS and inhibits polymerization of HbS, e.g., dosage, or different combinations of aptamer doses.

Pharmaceutical compositions suitable for oral administration include push-fit capsules made of gelatin, as well as soft, sealed capsules made of gelatin and a coating, e.g., a plasticizer, such as glycerol or sorbitol. The push-fit capsules can contain active ingredients admixed with a filler or binder, such as lactose or starches, lubricants, such as talc or magnesium stearate, and, optionally, stabilizers. In soft capsules, the aptamer that specifically binds to HbS and inhibits polymerization of HbS can be dissolved or suspended in suitable liquids, such as fatty oils, liquid paraffin, or liquid polyethylene glycols (PEGs), with or without stabilizers. Stabilizers can be added as warranted.

In some embodiments, the presently disclosed pharmaceutical compositions can be administered by rechargeable or biodegradable devices. For example, a variety of slow-release polymeric devices have been developed and tested in vivo for the controlled delivery of drugs, including proteinacious biopharmaceuticals. Suitable examples of sustained release preparations include semipermeable polymer matrices in the form of shaped articles, e.g., films or microcapsules. Sustained release matrices include polyesters, hydrogels, polylactides (U.S. Pat. No. 3,773,919; EP 58,481), copolymers of L-glutamic acid and gamma ethyl-L-glutamate (Sidman et al., Biopolymers 22:547, 1983), poly (2-hydroxyethyl-methacrylate) (Langer et al., J. Biomed. Mater. Res. 15:167, 1981; Langer, Chem. Tech. 12:98, 1982), ethylene vinyl acetate (Langer et al., Id), or poly-D-(−)-3-hydroxybutyric acid (EP 133,988A). Sustained release compositions also include liposomally entrapped aptamers, which can be prepared by methods known per se (Epstein et al., Proc. Natl. Acad. Sci. U.S.A. 82:3688, 1985; Hwang et al., Proc. Natl. Acad. Sci. U.S.A. 77:4030, 1980; U.S. Pat. Nos. 4,485,045 and 4,544,545; and EP 102,324A). Ordinarily, the liposomes are of the small (about 200-800 Angstroms) unilamelar type in which the lipid content is greater than about 30 mol % cholesterol, the selected proportion being adjusted for the optimal therapy. Such materials can comprise an implant, for example, for sustained release of the presently disclosed aptamers that specifically bind to HbS and inhibit polymerization of HbS, which, in some embodiments, can be implanted at a particular, pre-determined target site.

Pharmaceutical compositions for parenteral administration include aqueous solutions of aptamers that specifically bind to HbS and inhibit polymerization of HbS. For injection, the presently disclosed pharmaceutical compositions can be formulated in aqueous solutions, for example, in some embodiments, in physiologically compatible buffers, such as Hank's solution, Ringer's solution, or physiologically buffered saline. Aqueous injection suspensions can contain substances that increase the viscosity of the suspension, such as sodium carboxymethyl cellulose, sorbitol, or dextran. Additionally, suspensions of the aptamers that specifically bind to HbS and inhibit polymerization of HbS or vehicles include fatty oils, such as sesame oil, or synthetic fatty acid esters, such as ethyl oleate or triglycerides, or liposomes. Optionally, the suspension also can contain suitable stabilizers or agents that increase the solubility of the aptamers that specifically bind to HbS and inhibit polymerization of HbS to allow for the preparation of highly concentrated solutions.

For nasal or transmucosal administration generally, penetrants appropriate to the particular barrier to be permeated are used in the formulation. Such penetrants are generally known in the art.

For inhalation delivery, the agents of the disclosure also can be formulated by methods known to those of skill in the art, and may include, for example, but not limited to, examples of solubilizing, diluting, or dispersing substances such as, saline, preservatives, such as benzyl alcohol, absorption promoters, and fluorocarbons.

Additional ingredients can be added to compositions for topical administration, as long as such ingredients are pharmaceutically acceptable and not deleterious to the epithelial cells or their function. Further, such additional ingredients should not adversely affect the epithelial penetration efficiency of the composition, and should not cause deterioration in the stability of the composition. For example, fragrances, opacifiers, antioxidants, gelling agents, stabilizers, surfactants, emollients, coloring agents, preservatives, buffering agents, and the like can be present. The pH of the presently disclosed topical composition can be adjusted to a physiologically acceptable range of from about 6.0 to about 9.0 by adding buffering agents thereto such that the composition is physiologically compatible with a subject's skin.

In other embodiments, the pharmaceutical composition can be a lyophilized powder, optionally including additives, such as 1 mM-50 mM histidine, 0.1%-2% sucrose, 2%-7% mannitol at a pH range of 4.5 to 5.5 that is combined with buffer prior to use.

The presently disclosed subject matter also includes the use of aptamers that specifically bind to HbS and inhibit polymerization of HbS disclosed herein, in the manufacture of a medicament for sickle cell disease.

Regardless of the route of administration selected, the presently disclosed aptamers that specifically bind to HbS and inhibit polymerization of HbS, which may be used in a suitable hydrated form, and/or the pharmaceutical compositions are formulated into pharmaceutically acceptable dosage forms such as described below or by other conventional methods known to those of skill in the art.

The term "effective amount," as in "a therapeutically effective amount," of a therapeutic agent refers to the amount of the agent necessary to elicit the desired biological response. As will be appreciated by those of ordinary skill in this art, the effective amount of an agent may vary depending on such factors as the desired biological endpoint, the agent to be delivered, the composition of the pharmaceutical composition, the target tissue or cell, and the like. More particularly, the term "effective amount" refers to an amount sufficient to produce the desired effect, e.g., to reduce or ameliorate the severity, duration, progression, or onset of a disease, disorder, or condition (e.g., a disease, condition, or disorder related to polymerization of HbS such as sickle cell disease), or one or more symptoms thereof; prevent the advancement of a disease, disorder, or condition, cause the regression of a disease, disorder, or condition; prevent the recurrence, development, onset or progression of a symptom associated with a disease, disorder, or condition, or enhance or improve the prophylactic or therapeutic effect(s) of another therapy.

Actual dosage levels of the active ingredients in the presently disclosed pharmaceutical compositions can be varied so as to obtain an amount of the active ingredient that is effective to achieve the desired therapeutic response for a particular subject, composition, route of administration, and disease, disorder, or condition without being toxic to the subject. The selected dosage level will depend on a variety of factors including the activity of the particular aptamer employed, the route of administration, the time of administration, the rate of excretion of the particular aptamer being employed, the duration of the treatment, other drugs, aptamers and/or materials used in combination with the particular aptamer employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the aptamers that specifically bind to HbS and inhibit polymerization of HbS, employed in the pharmaceutical composition at levels lower than that required to achieve the desired therapeutic effect and gradually increase the dosage until the desired effect is achieved. Accordingly, the dosage range for administration will be adjusted by the physician as necessary. It will be appreciated that an amount of an aptamer required for achieving the desired biological response, e.g., inhibition of polymerization of HbS, may be different from the amount of compound effective for another purpose.

In general, a suitable daily dose of aptamers that specifically bind to HbS and inhibit polymerization of HbS, will be that amount of the aptamer that is the lowest dose effective to produce a therapeutic effect. Such an effective dose will generally depend upon the factors described above. Generally, doses of the aptamers that specifically bind to HbS and inhibit polymerization of HbS will range from about 0.0001 to about 1000 mg per kilogram of body weight of the subject per day. In certain embodiments, the dosage is between about 1 µg/kg and about 500 mg/kg, more preferably between about 0.01 mg/kg and about 50 mg/kg. For example, in certain embodiments, a dose can be about 1, 5, 10, 15, 20, or 40 mg/kg/day.

If desired, the effective daily dose of the aptamers that specifically bind to HbS and inhibit polymerization of HbS can be administered as two, three, four, five, six or more sub-doses administered separately at appropriate intervals throughout the day, optionally, in unit dosage forms.

D. Kits or Pharmaceutical Systems

The presently disclosed aptamers that specifically bind to HbS and inhibit polymerization of HbS disclosed herein and compositions can be assembled into kits or pharmaceutical systems for use in treating or preventing neurodegenerative diseases, disorders, or conditions. In some embodiments, the presently disclosed kits or pharmaceutical systems include aptamers that specifically bind to HbS and inhibit polymerization of HbS as disclosed herein. In particular embodiments, the aptamers that specifically bind to HbS and inhibit polymerization of HbS as disclosed herein, are in unit dosage form. In further embodiments, the aptamers that specifically bind to HbS and inhibit polymerization of HbS as disclosed herein, can be present together with a pharmaceutically acceptable solvent, carrier, excipient, or the like, as described herein.

In some embodiments, the presently disclosed kits comprise one or more containers, including, but not limited to a vial, tube, ampule, bottle and the like, for containing the compound. The one or more containers also can be carried within a suitable carrier, such as a box, carton, tube or the like. Such containers can be made of plastic, glass, laminated paper, metal foil, or other materials suitable for holding medicaments.

In some embodiments, the container can hold a composition that is by itself or when combined with another composition effective for treating or preventing the condition and may have a sterile access port (for example the container may be an intravenous solution bag or a vial having a stopper pierceable by a hypodermic injection needle). Alternatively, or additionally, the article of manufacture may further include a second (or third) container including a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The presently disclosed kits or pharmaceutical systems also can include associated instructions for using the aptamers that specifically bind to HbS and inhibit polymerization of HbS as disclosed herein for treating or sickle cell disease. In some embodiments, the instructions include one or more of the following: a description of the aptamer that specifically binds to HbS and inhibits polymerization of HbS as disclosed herein; a dosage schedule and administration for treating or preventing sickle cell disease; precautions; warnings; indications; counter-indications; overdosage information; adverse reactions; animal pharmacology; clinical studies; and references. The instructions can be printed directly on a container (when present), as a label applied to the container, as a separate sheet, pamphlet, card, or folder supplied in or with the container.

IV. Antidotes

The presently disclosed subject matter also relates to antidotes for the aptamers that specifically bind to HbS and inhibit polymerization of HbS as disclosed herein. Such antidotes can comprise oligonucleotides that are reverse complements of segments of the aptamers that specifically bind to HbS and inhibit polymerization of HbS as disclosed herein. In accordance with the presently disclosed subject matter, the antidote is contacted with a targeted aptamer under conditions such that it binds to the aptamer and modifies the interaction between the aptamer and its target molecule (e.g., HbS). Modification of that interaction can result from modification of the aptamer structure as a result of binding by the antidote. The antidote can bind free aptamer and/or aptamer bound to its target molecule. In certain embodiments, the aptamer that specifically binds to HbS and inhibits polymerization of HbS as disclosed herein is provided in alternation with an antidote.

Antidotes of the presently disclosed subject matter can be designed so as to bind any particular aptamer with a high degree of specificity and a desired degree of affinity. The antidote can be designed so that upon binding to the targeted aptamer, the three-dimensional structure of that aptamer is altered such that the aptamer can no longer bind to its target molecule or binds to its target molecule with less affinity.

Antidotes of the presently disclosed subject matter include any pharmaceutically acceptable agent that can bind an aptamer and modify the interaction between that aptamer and its target molecule (e.g., by modifying the structure of the aptamer) in a desired manner. Examples of such antidotes include oligonucleotides complementary to at least a portion of the aptamers that specifically bind to HbS and inhibit polymerization of HbS as disclosed herein (including ribozymes or DNAzymes or peptide nucleic acids), nucleic acid binding peptides, polypeptides or proteins including nucleic acid binding tripeptides (see generally, Hwang et al. (1999) *Proc. Natl. Acad. Sci. USA* 96:12997), and oligosaccharides such as aminoglycosides (see, generally, Davies et al. (1993) Chapter 8, p. 185, RNA World, Cold Spring Harbor Laboratory Press, eds Gestlaad and Atkins; Werstuck et al. (1998) *Science* 282:296; U.S. Pat. Nos. 5,935,776 and 5,534,408; Chase et al. (1986) *Ann. Rev. Biochem.* 56:103; Eichhorn et al. (1968) *J. Am. Chem. Soc.* 90:7323; Dale et al. (1975) *Biochemistry* 14:2447; and Lippard et al. (1978) *Acc. Chem. Res.* 11:211).

Standard binding assays can be used to screen for antidotes of the presently disclosed subject matter (e.g., using BIACORE assays). Candidate antidotes can be contacted with the aptamer to be targeted under conditions favoring binding and a determination made as to whether the candidate antidote in fact binds the aptamer. Candidate antidotes that are found to bind the aptamer can then be analyzed in an appropriate bioassay (which will vary depending on the aptamer and its target molecule) to determine if the candidate antidote can affect the binding of the aptamer to its target molecule.

Where the antidote is an oligonucleotide, the antidote oligonucleotide does not need to be completely complementary to the aptamer that specifically binds to HbS and inhibits polymerization of HbS as disclosed herein as long as the antidote sufficiently binds to or hybridizes to the aptamer to neutralize its activity. In one embodiment, the antidote of the presently disclosed subject matter is an oligonucleotide that comprises a sequence complementary to at least a portion of the targeted aptamer sequence. In one embodiment, the antidote oligonucleotide comprises a sequence complementary to up to 80, 75, 70, 65, 60, 55, 50, 45, 40, 35, 30, 25, 20, 15, 10, or 5 consecutive nucleotides of the targeted aptamer.

V. Diagnostic Methods

In one embodiment, the presently disclosed subject matter provides a method for diagnosing or predicting a sickle cell disease in a subject having or at risk of developing a sickle cell disease or at risk of passing it on to offspring. The method includes contacting a biological sample from the subject with an aptamer that specifically binds to HbS and inhibits polymerization of HbS as disclosed herein.

The aptamers that specifically bind to HbS and inhibit polymerization of HbS as disclosed herein are particularly well suited for diagnostic applications. Aptamers represent a class of molecules that may be used in place of antibodies for in vitro or in vivo diagnostic purposes. The aptamers of the presently disclosed subject matter are therefore particularly useful as diagnostic reagents to detect the presence or absence of the target substances to which they specifically bind, i.e., HbS. Such diagnostic tests are conducted by contacting a biological sample with the specifically binding oligonucleotide to obtain a complex which is then detected by conventional means. For example, the aptamers may be labeled using radioactive, fluorescent, or chromogenic labels and the presence of label bound to solid support to which the target substance has been bound through a specific or nonspecific binding means detected. Alternatively, the specifically binding oligonucleotides may be used to effect initial complexation to the support. Means for conducting assays using such oligomers as specific binding partners will track those for standard specific binding partner based assays.

Accordingly, in one embodiment, the presently disclosed subject matter provides a method for diagnosing or predicting a sickle cell disease in a subject having or at risk of developing a sickle cell disease or at risk of passing it on to offspring, the method comprising: (a) obtaining a biological sample from the subject; (b) contacting the biological sample with a polynucleotide aptamer that specifically binds to HbS as disclosed herein; and (c) detecting binding of the polynucleotide aptamer with HbS in the biological sample, wherein detection of binding of the polynucleotide aptamer with HbS in the biological sample is indicative of the subject having or at risk of developing a sickle cell disease or at risk of passing it on to offspring. The aptamers can be labeled for detection using methods and labels known in the art including, but not limited to, fluorescent, luminescent, phosphorescent, radioactive, and/or colorimetric compounds.

As used herein, the phrase "biological sample" encompasses a variety of sample types obtained from a subject and useful in the procedure of the presently disclosed subject matter. In one embodiment of the presently disclosed subject matter, the biological sample comprises whole blood, hemocytes, serum, or plasma. However, biological samples may include, but are not limited to, solid tissue samples, liquid tissue samples, biological fluids, aspirates, cells and cell fragments. Specific examples of biological samples include, but are not limited to, solid tissue samples obtained by surgical removal, pathology specimens, archived samples, or biopsy specimens, tissue cultures or cells derived therefrom and the progeny thereof, and sections or smears prepared from any of these sources. Non-limiting examples of biological samples include samples obtained from breast tissue, lymph nodes, and breast tumors. Biological samples also include any material derived from the body of a vertebrate animal, including, but not limited to, blood, cerebrospinal fluid, serum, plasma, urine, nipple aspirate, fine needle aspirate, tissue lavage such as ductal lavage, saliva, sputum, ascites fluid, liver, kidney, breast, bone, bone marrow, testes, brain, ovary, skin, lung, prostate, thyroid, pancreas, cervix, stomach, intestine, colorectal, brain, bladder, colon, nares, uterine, semen, lymph, vaginal pool, synovial fluid, spinal fluid, head and neck, nasopharynx tumors, amniotic fluid, breast milk, pulmonary sputum or surfactant, urine, fecal matter and other liquid samples of biologic origin.

VI. Capture Reagents

In another embodiment, the presently disclosed subject matter relates to the use of aptamers that specifically bind to HbS as capture reagents for clearing clear HbS or other hemoglobins (including normal hemoglobin) from a biological sample. Within these methods of the invention, the aptamers that specifically bind to HbS do not necessarily need to also inhibit polymerization of HbS.

Accordingly, in one embodiment the presently disclosed subject matter is directed to a method of purifying hemoglobin from a biological sample comprising providing a biological sample containing hemoglobin, contacting the biological sample with an aptamer that specifically binds to HbS as disclosed herein under conditions effective to bind hemoglobin to the aptamer, and recovering the hemoglobin bound to the aptamer. In certain embodiments, the hemoglobin is HbS. In other embodiments, the biological sample comprises whole blood, hemocytes, serum, or plasma.

The methods for purifying hemoglobin from a biological sample may include the use of a solid support comprising an immobilized aptamer. Thus, in one embodiment of the method of purifying hemoglobin from a biological sample, the step of contacting the biological sample with an aptamer that specifically binds to HbS as disclosed herein under conditions effective to bind hemoglobin to the aptamer comprises providing a solid support comprising an aptamer that specifically binds to HbS as disclosed herein immobilized onto the solid support through a spacer.

As used herein, a "spacer" is intended to mean a molecule which is inserted between the aptamer and the solid support. Advantageously, the spacer is bound both to one end of the aptamer and to the solid support. Advantageously, such structure comprising a spacer does not immobilize directly the aptamer onto the solid support. The nature of the spacer may be chosen according to the knowledge of one skilled in the art; for example the spacer may be a non specific oligonucleotide sequence or may be polyethylene glycol (PEG). When the spacer is a non specific oligonucleotide sequence, said sequence may contain at least 5 nucleotides, particularly between 5 and 15 nucleotides.

For immobilizing the aptamer onto a spacer, the aptamer may be chemically modified with various chemical groups such as groups enabling to covalently immobilize the aptamer, such as thiols, amines or any other group that could react with chemical groups present on the support or groups enabling to non-covalently immobilize the aptamer, such as the biotin-streptavidin system. These techniques may also be used for immobilizing the spacer onto the solid support.

Once immobilized onto the solid support via the spacer, the aptamer may be modified at the free end thereof (i.e. the end that is not bound to the spacer) by, without limitation, a chemically modified nucleotide (such as 2' omethyl or 2' fluoropyrimidine, 2' ribopurine, phosphoramidite), a reversed nucleotide or a chemical group (PEG, polycations, cholesterol). These and other modifications to the presently disclosed aptamers as disclosed elsewhere herein may be used to protect the aptamer against enzymatic degradation.

The solid support may be an affinity chromatography column containing a gel derived from agarose or cellulose or a synthetic gel such as an acrylamide, a methacrylate or a polystyrene derivative; a chip such as a chip adapted for surface plasmon resonance; a membrane such as a polyamide, a polyacrylonitrile or a polyester membrane; a magnetic or paramagnetic bead.

VII. Rational Drug Design

In another embodiment, the presently disclosed subject matter relates to the use of an aptamer that specifically binds to HbS and inhibits polymerization of HbS as disclosed herein as a template for rational drug design.

For example, structures of RNA aptamers that recognize the shape of HbS could be determined by spectroscopy or X-ray crystallography. These structures could be used to guide the rational design of drugs (mimetics) that would recognize and bind to HbS and inhibit polymerization of HbS.

Accordingly, in one embodiment the presently disclosed subject matter is directed to a method of using a three-dimensional structure of an aptamer that specifically binds to HbS and inhibits polymerization of HbS as disclosed herein in a drug screening assay comprising:

(a) selecting a potential drug by performing rational drug design with the three-dimensional structure of the polynucleotide aptamer that specifically binds to HbS and inhibits polymerization of HbS determined from one or more sets of atomic coordinates; wherein said selecting is performed in conjunction with computer modeling;

(b) contacting the potential drug with HbS;

(c) detecting the binding of the potential drug with the HbS; and (d) detecting the inhibition of polymerization of HbS by the potential drug; wherein a potential drug is selected as a drug if the potential drug binds to HbS and inhibits polymerization of HbS.

Alternatively, a refined aptamer sequence can be elucidated by modifying a known aptamer structure using software comprising "builder" type algorithms which utilizes a set of atomic coordinates defining a three-dimensional structure of the binding pocket and the three-dimensional structures of the known aptamer to computationally assemble a refined aptamer. Ample guidance for performing rational drug design via software employing such "scanner" and "builder" type algorithms is available in the literature of the art (e.g., Halperin et al. (2002) *Proteins* 47:409-43; Gohlke & Klebe (2001) *Curr Opin Struct Biol.* 11:231-5; Zeng (2000) *Comb. Chem. High Throughput Screen.* 3:355-62).

Criteria that may be employed by software programs used in rational drug design to qualify the binding of screened aptamer structures with binding pockets and/or binding sites of HbS include gap space, hydrogen bonding, electrostatic interactions, van der Waals forces, hydrophilicity/hydrophobicity, etc. Generally, the greater the contact area between the screened aptamer and the HbS binding region, the lower the steric hindrance, the lower the "gap space", the greater the number of hydrogen bonds, and the greater the sum total of the van der Waals forces between the screened aptamer and the HbS binding region, the greater will be the capacity of the screened aptamer to bind with the target HbS. The "gap space" refers to unoccupied space between the van der Waals surface of a screened aptamer positioned within a binding pocket or site and the surface of the binding pocket or site defined by amino acid residues in the binding pocket or site. Gap space may be identified, for example, using an algorithm based on a series of cubic grids surrounding the docked molecule, with a user-defined grid spacing, and represents volume that could advantageously be occupied by a modifying the docked aptamer positioned within the binding region of the HbS.

Contact area between compounds may be directly calculated from the coordinates of the compounds in docked conformation using the MS program (Connolly (1983) *Science* 221:709-713).

Suitable software employing "scanner" type algorithms include, for example, docking software such as GRAM, DOCK, or AUTODOCK (reviewed in Dunbrack et al. (1997) *Folding and Design* 2:27), AFFINITY software of the INSIGHTII package (Molecular Simulations Inc., 1996, San Diego, Calif.), GRID (Goodford (1985) *J. Med. Chem.* 28:849-857; GRID is available from Oxford University, Oxford, UK), and MCSS (Miranker & Karplus (1991) *Proteins: Structure Function and Genetics* 11:29-34; MCSS is available from Molecular Simulations, Burlington, Mass.).

The AUTODOCK program (Goodsell & Olson (1990) *Proteins: Struct Funct Genet.* 8:195-202; available from Scripps Research Institute, La Jolla, Calif.) helps in docking screened molecules to binding pockets in a flexible manner using a Monte Carlo simulated annealing approach. The procedure enables a search without bias introduced by the researcher. This bias can influence orientation and conformation of a screened molecule in the targeted binding pocket The DOCK program (Kuntz et al. (1982) *J. Mol. Biol.* 161:269-288; available from University of California, San Francisco), is based on a description of the negative image of a space-filling representation of the binding pocket, and includes a force field for energy evaluation, limited conformational flexibility and consideration of hydrophobicity in the energy evaluation.

Modeling or docking may be followed by energy minimization with standard molecular mechanics force fields or dynamics with programs such as CHARMM (Brooks et al. (1983) *J. Comp. Chem.* 4:187-217) or AMBER (Weiner et al. (1984) *J. Am. Chem. Soc.* 106:765-784). As used herein, "minimization of energy" means achieving an atomic geometry of a chemical structure via systematic alteration such that any further minor perturbation of the atomic geometry would cause the total energy of the system as measured by a molecular mechanics force-field to increase. Minimization and molecular mechanics force fields are well understood in computational chemistry (e.g., Burkert & Allinger, "Molecular Mechanics", ACS Monograph 177, pp. 59-78, American Chemical Society, Washington, D.C. (1982)).

Programs employing "builder" type algorithms include LEGEND (Nishibata & Itai (1991) *Tetrahedron* 47:8985; available from Molecular Simulations, Burlington, Mass.), LEAPFROG (Tripos Associates, St. Louis, Mo.), CAVEAT (Bartlett et al. (1989) *Special Pub Royal Chem Soc.* 78:182-196; available from University of California, Berkeley), HOOK (Molecular Simulations, Burlington, Mass.), and LUDI (Bohm (1992) *J. Comp. Aid Molec. Design* 6:61-78; available from Biosym Technologies, San Diego, Calif.).

The CAVEAT program suggests binding molecules based on desired bond vectors. The HOOK program proposes docking sites by using multiple copies of functional groups in simultaneous searches. LUDI is a program based on fragments rather than on descriptors which proposes somewhat larger fragments to match with a binding pocket and scores its hits based on geometric criteria taken from the Cambridge Structural Database (CSD), the Protein Data Bank (PDB) and on criteria based on binding data. LUDI may be advantageously employed to calculate the inhibition constant of a docked chemical structure. Inhibition constants (Ki values) of compounds in the final docking positions can be evaluated using LUDI software.

During or following rational drug design, docking of an intermediate chemical structure or of an aptamer with the HbS binding pocket or site may be visualized via structural models, such as three-dimensional models, thereof displayed on a computer screen, so as to advantageously allow user intervention during the rational drug design to optimize a chemical structure.

Software programs useful for displaying such three-dimensional structural models, include RIBBONS (Carson (1997) *Methods in Enzymology* 277:25), O (Jones et al. (1991) *Acta Crystallogr.* A47:110), DINO; and QUANTA, INSIGHT, SYBYL, MACROMODE, ICM, MOLMOL, RASMOL and GRASP (reviewed in Kraulis (1991) *Appl Crystallogr.* 24:946).

Other molecular modeling techniques may also be employed in accordance with the presently disclosed subject matter (e.g., Cohen et al. (1990) *J. Med. Chem.* 33:883-894; Navia & Murcko (1992) *Current Opinions in Structural Biology* 2:202-210). For example, where the structures of test compounds are known, a model of the test compound may be superimposed over the model of the structure of the aptamers as disclosed herein. Numerous methods and techniques are known in the art for performing this step, any of which may be used (e.g., Farmer "Drug Design", Ariens (ed.), Vol. 10, pp 119-143 (Academic Press, New York, 1980); U.S. Pat. Nos. 5,331,573; 5,500,807; Verlinde (1994) *Structure* 2:577-587; and Kuntz (1992) *Science* 257:1078-108).

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

The primary aim of the present study was to generate one or more RNA aptamers that would bind sickle hemoglobin (HbS) in such a way that polymerization of HbS would be inhibited, without a deleterious effect on hemoglobin's functional capabilities. Preventing the polymerization of HbS would essentially cure sickle cell anemia, since the complications of the disease arise directly as a result of red blood cell changes brought about by HbS polymerization. Because it is the deoxygenated form of HbS that polymerizes, the creation and characterization of aptamers to deoxyHbS were conducted first. However, aptamers to oxyHbS were also created and characterized in an effort to cast a large net and limit assumptions about which type of aptamers may be more effective ultimately in preventing polymerization. Additionally, aptamers that specifically bind HbS but do not have any effect on polymerization might be useful as reagents for other scientific studies. For example, these could be used to clear HbS or other hemoglobins (including normal hemoglobin) from plasma for proteomic studies or be used to identify the presence of HbS in a patient sample, or for therapeutics.

To accomplish these goals, the "systematic evolution of ligands by exponential enrichment" (SELEX) process was used to select for aptamers that bind specifically to HbS in either its oxygenated or deoxygenated states. Each aptamer pool was analyzed for its ability to bind both oxy-HbS and deoxy-HbS at different rounds in the selection process. However, both positive and negative selection were used, including experiments where the bound aptamers was recovered from the target, and experiments where the aptamers that recognized more than one target were removed from the pool (for example, by absorbing pools of molecules that bind both HbA and HbS to HbA, allowing the molecules that bind only to S to "flow through.") Once a relatively small pool of high affinity aptamers was obtained, individual aptamers were then amplified and tested for their ability to inhibit polymerization in a closed anaerobic system, in which sodium dithionite was used to deoxygenate hemoglobin.

Materials and Methods

Preparation of Hemoglobin

After obtaining informed consent, venous blood was drawn from an untransfused patient with homozygous SS disease. Red cells were washed 5 times with PBS, hemolyzed in 3.5 volumes of distilled water, and stromata were removed by centrifugation at 20,000 g for 25 minutes. Hemoglobin-rich extract was dialyzed into 0.05M tris-Cl, pH 8.3, and purified HbS was obtained by separation on a DEAE Sephadex A-50 anion exchange column, developing with a gradient of 0.05M Tris-HCl, pH 8.3 to 0.05M Tris-HCl pH 7.3. The HbS was dialyzed against 2 mM HEPES, pH 7.4 for the SELEX process and against 1M potassium phosphate buffer, pH 7.1 for use in the polymerization assays, and stored in small aliquots at −80° C. Hemoglobin concentrations were determined by standard methods. When necessary, hemoglobin was concentrated with Amicon Ultra 30K centrifugal filters (Millipore, Billerica, Mass.). Proportions of hemoglobins at different oxidation states within a solution were determined by the method of Benesch, Benesch and Yung (Benesch, Benesch, & Yung (1973) *Anal Biochem.* 55:245-248).

Selection of Aptamers Through Systematic Evolution of Ligands by Exponential Enrichment (SELEX)

The initial oligonucleotide library was the Sel2 library (Trilink Biotechnologies, San Diego, Calif.) comprising the sequence 5'-GGGAGGACGAUGCGG($N_{40}$)-CAGACGA-CUCGCUGAGGAUCCGAGA-3' (SEQ ID NO:1), where N40 represents a random sequence of 40 nucleotides. Template DNA was synthesized with the Klenow fragment of DNA polymerase I (New England Biolabs, Ipswich, Mass.). Two separate selections were performed. Both selections shared the first four rounds, which were carried out as described below, using deoxygenated HbS as the target protein. For these rounds, binding was carried out at 37° for 5 minutes. After round 4, the resulting RNA pool was utilized to continue with two separate selections. The first targeted HbS in its oxygenated state. Measurements of the oxidation states of HbS in a freshly-thawed aliquot showed approximately 83-95% to be oxygenated hemoglobin, so freshly thawed HbS was used in the binding steps. Incubation was carried out at room temperature for 10 minutes at a ratio of 5 moles RNA per mole of protein in round 5, increasing to 9 moles RNA per mole of protein by round 14. Bound RNA was collected by capturing the protein on a nitrocellulose membrane, eluting and extracting the RNA. RT-PCR reactions were performed on the eluted RNA with AMV Reverse Transcriptase (Roche, Indianapolis, Ind.) and Platinum Taq Polymerase (Invitrogen, Grand Island, N.Y.). Transcription was performed with the Durascribe T7 kit (Epicentre, Madison, Wis.), which incorporates the modified nucleotides 2'-fluorine-dCTP and 2'-fluorine-dUTP into the sequences to generate nuclease-resistant RNA.

The second selection targeted deoxygenated HbS. Paired rounds were performed in which cycles of selection against deoxy-HbS were alternated with cycles of subtractive binding with oxy-HbS, described below. In order to deoxygenate the HbS prior to incubation, it was thawed, exposed to a vacuum by injection into a vacuum tube with a septum cap, and rocked at room temperature for 1 hour. The hemoglobin was then removed from the tube, and incubation with RNA aptamer library was immediately carried out at room temperature for 10 minutes at a ratio of 3 moles RNA per mole of protein in round 1 then stepwise up to 7 moles RNA per mole protein by round 9. For subtractive binding, the oligo pool was incubated with oxy-HbS at room temperature for 10 minutes and the unbound flow-through material was collected and saved, following protein capture on a nitrocellulose membrane. Butanol extraction was employed to concentrate the unbound oligos. Subtractive binding followed by standard binding was done for multiple "paired" rounds, with RNA ratios for the oxy-HbS rounds similar to those for the deoxy-HbS rounds, except for the final cycle of subtractive binding, in which the ratio was 5 moles RNA per mole protein. This lower ratio allowed the oxygenated protein to bind and retain a higher fraction of oxy-HbS-targetted aptamers in the pool. Oxy-HbS oligo selection rounds 1-7 and deoxy-HbS oligo selection rounds 1-5 were performed in low salt binding buffer (20 mM HEPES pH 7.4, 50 mM NaCl, 2 mM $CaCl_2$, 0.01% BSA) and low salt wash buffer (20 mM HEPES pH 7.4, 50 mM NaCl, 2 mM $CaCl_2$). Oxy-HbS selection rounds 8-14 and deoxy-HbS selection rounds 6-9 were performed in high salt binding buffer (20 mM HEPES pH 7.4, 150 mM NaCl, 2 mM $CaCl_2$, 0.01% BSA) and high salt wash buffer (20 mM HEPES pH 7.4, 150 mM NaCl, 2 mM $CaCl_2$). The last cycle of subtractive binding for deoxy-HbS aptamers, using oxy-HbS as the target, was done in low salt buffers, again to decrease the stringency of aptamer-protein binding.

Binding Assays

Aptamers were dephosphorylated with bacterial alkaline phosphatase (Invitrogen, Grand Island, N.Y.) and 5' end-labelled with $\alpha$-$^{32}$P-ATP (Perkin Elmer, Waltham, Mass.) using T4 polynucleotide kinase (New England Biolabs, Ipswich, Mass.). RNA was diluted to 2,000 cpm/ul in the appropriate binding buffer and heated at 65° C. for 5 minutes. For the oligomer pool targeting oxyHbS, the hemoglobin was thawed and used to make a dilution series in binding buffer. For the oligo pool targetting deoxyHbS the hemoglobin was thawed, exposed to a vacuum and rocked at room temperature for 1 hour, and used immediately to make a dilution series in binding buffer. For both assays, 5 ul of labeled RNA (10,000 cpm) was added to each tube of the dilution series, such that the final protein concentrations ranged from 0.078 uM to 10 uM, in 2-fold increments. Each mixture was incubated (at 37° C. for 5 minutes for rounds 0 and 4, and at room temperature for 10 minutes for subsequent rounds) and passed over a nitrocellulose membrane to capture the HbS and bound RNA, with the non-bound RNA captured on a nylon membrane. The fractions of bound and unbound RNA were quantified with a Beckman LS-3801 scintillation counter, and the nonspecific binding subtracted.

Cloning, Sequencing and RNA Preparation

At rounds 7 and 9 of selection targeting deoxy-HbS and rounds 11 and 14 of selection targeting oxy-HbS, cDNA was synthesized from RNA and used for cloning and sequencing of individual aptamers. DNA oligos were ligated into the pCR2.1-TOPO vector using the TOPO cloning kit (Invitrogen, Grand Island, N.Y.) and T4 DNA ligase (New England Biolabs, Ipswich, Mass.). Transformations were performed using One Shot TOP10 cells (Invitrogen, Grand island, NY), and following overnight growth, mini-preps were performed with the Qiaprep spin miniprep kit (Qiagen, Valencia, Calif.) to produce DNA for sequencing. Sequencing was carried out at the Johns Hopkins Genetic Resources Core Facility. Large quantities of aptamer for analysis were generated from clone DNA by transcription using the Durascribe T7 kit (Epicentre, Madison, Wis.). RNA was purified by running on a 12% denaturing gel and eluted in $dH_2O$.

Polymerization Assays

Sickle hemoglobin in 1 M potassium phosphate buffer, pH 7.1 was thawed on ice, concentrated in an Amicon Ultra 30K centrifugal filter tube (Millipore, Billerica, Mass.) at 4° C. and kept on ice. Aptamers in distilled $H_2O$ or $H_2O$ alone as a control were thawed on ice, aliquoted into tubes for each individual replicate, heated at 65° C. for 5 minutes, and placed on ice. SM20, a non-related aptamer targeting the plasminogen activator inhibitor-1 (PAI-1) and possessing flanking sequences identical to those generated here, was used as a negative aptamer control. To deoxygenate sodium dithionite powder (Sigma, St. Louis, Mo.), it was placed in a tube with a rubber septum cap and flushed with nitrogen gas by inserting one needle for gas inlet and one needle for gas outlet into the cap (Adachi & Asakura (1979) *J. Biol. Chem.* 254:7765-7771). A buffer solution of 1.6 M potassium phosphate buffer pH 7.8 was deoxygenated similarly in separate tubes flushed with nitrogen gas. The dithionite powder and buffer were exposed to nitrogen for 1½ hours, flushing with new nitrogen gas every ½ hour, then placed on ice. Sodium dithionite stock solution and subsequent dilutions were then made using a Hamilton gas-tight syringe to transfer buffer from one tube to another (Adachi & Asakura (1979) *J. Biol. Chem.* 254:7765-7771). Each replicate was run in a closed 1 cm quartz cuvette (Starna Cells, Atascadero, Calif.) that had been flushed with nitrogen gas through a septum cap as described above, and placed on ice. Cold 1.6 M potassium phosphate buffer pH, 7.8 and HbS were added to the tube containing aptamer, mixed well, and added to the nitrogen-filled cuvette using a Hamilton gas-tight syringe. The syringe was immediately washed and used to transfer sodium dithionite solution from its dilution tube into the cuvette. The final concentrations of all components in the cuvette were 0.12 mM HbS, 0.48 mM sodium dithionite, and 0.01 mM aptamer in 1.49 M potassium phosphate, pH 7.9. After addition of dithionite, the contents were briefly mixed and put in a 37° C. water bath. The cuvette was removed one minute after incubation began and turbidity measured with a Beckman DU-640B spectrophotometer (Beckman Coulter, Inc., Brea, Calif.) at a wavelength of 700 nm (Adachi & Asakura (1979) *J. Biol. Chem.* 254:7765-7771; Harrington (1998) *Comp. Biochem. Physiol.* 119B(2):305-309; Eaton & Hofrichter (1987) *Blood* 70:1245-1266; Knee & Mukerji (2009) *Biochemistry* 48:9903-9911; Magdoff-Fairchild et. al. (1976) *Proc. Nat. Acad. Sci.* 73(4):990-994). Measurements were also taken at 540, 560 and 576 nm in order to calculate the fractions of HbS in various oxygenation states. After the spectrophotometric measurement, the cuvette was immediately returned to 37° C. Subsequent readings were done in a similar manner every 3 minutes through the 34 minute time point, then every 5 minutes from the 40 minute to the 70 minute time points.

Results

Different Sets of Aptamers Generated Targeting Oxy-HbS Versus Deoxy-HbS

One of the goals of the present study was to generate aptamers that bind to HbS in either its oxygenated or deoxygenated states specifically and further to identify aptamers that when bound result in inhibition of polymerization of deoxy-HbS. While aptamers binding selectively to oxy- or deoxyhemoglobin were targeted, it was also recognized that aptamers binding to both oxygenated and deoxygenated Hb would likely be identified and would be of value, potentially inhibiting HbS polymerization as well. Clones were obtained and sequenced at rounds 11 and 14 of the oxy-HbS aptamer selection and rounds 7 and 9 of the deoxy-HbS aptamer selection. 57 total aptamers were identified that bound to deoxy-HbS. Of these, several aptamers were represented multiple times; many sequences were represented only once. 15 total aptamers were identified that bound oxy-HbS.

The unique sequences for the identified clones are shown in Table 1. Only one of the clones is represented in both the oxy and deoxy aptamer pool. Several aptamers identified in the group targeting deoxy-HbS were further amplified and analyzed for their ability to inhibit polymerization. Although the remainder of the discussion below applies to these deoxy-HbS aptamers that have been partially characterized for their anti-polymerization activity, all clones selected against both deoxy and oxy hemoglobin may potentially inhibit HbS polymerization as well.

TABLE 1

Complete Aptamer Sequences
(unique or representative of an identical family)

DeoxyHbS Aptamer Sequences

Clone deoxy 1 (SEQ ID NO: 2)
5' GGGAGGACGAUGCGGccgauuagaacugggcugcgaucggagauccucuagguuuCAGACGACUCGCUGAGGAUCCGAGA 3'

Clone deoxy 2 (SEQ ID NO: 3)
5' GGGAGGACGAUGCGGgccgagggauucgguguagacucugcacaguccugaaaagCAGACGACUCGCUGAGGAUCCGAGA 3'

Clone deoxy 3-A (SEQ ID NO: 4)
5' GGGAGGACGAUGCGGccgauuagaacugggcugaggcguucugcauuucggugauCAGACGACUCGCUGAGGAUCCGAGA 3'

Clone deoxy 3-B (SEQ ID NO: 5)
5' GGGAGGACGAUGCGGccgauuagaacugggcuguuccgacucugaauccggugauCAGACGACUCGCUGAGGAUCCGAGA 3'

TABLE 1-continued

Complete Aptamer Sequences
(unique or representative of an identical family)

```
Clone deoxy 5 (SEQ ID NO: 6)
5' GGGAGGACGAUGCGGuuggugaagggaggucagcauaucuucccgcgggaagcgaCGGACGACUCGCUGAGGAUCCGAGA 3'

Clone deoxy 7-A (SEQ ID NO: 7)
5' GGGAGGACGAUGCGGauccacggguaagggugagggacgacaucaaggcgagauuCAGACGACUCGCUGAGGAUCCGAGA 3'

Clone deoxy 8 (SEQ ID NO: 8)
5' GGGAGGACGAUGCGGuacgauuagaacuggugccgaacagcgcucguugaagacaCAGACGACUCGCUGAGGAUCCGAGA 3'

Clone deoxy 9 (SEQ ID NO: 9)
5' GGGAGGACGAUGCGGaggaaguaggguucguccauugggcgaguggccuguguuaCAGACGACUCGCUGAGGAUCCGAGA 3'

Clone deoxy 10 (SEQ ID NO: 10)
5' GGGAGGACGAUGCGGcacgguauaguggaguggguaggcaucgcucgacgagugaCAGACGACUCGCUGAGGAUCCGAGA 3'

Clone deoxy 15 (SEQ ID NO: 11)
5' GGGAGGACGAUGCGGgaguagggagguaaucgccaccccaacgcggagacagcgaCAGACGACUCGCUGAGGAUCCGAGA 3'

Clone deoxy 19-C-1 (SEQ ID NO: 12)
5' GGGAGGACGAUGCGGucgauaggggacggaccgcgcuggaaacucaacguagcaCAGACGACUCGCUGAGGAUCCGAGA 3'

Clone deoxy 20 (SEQ ID NO: 13)
5' GGGAGGACGAUGCGGcacugaugggagugggaucagugucgagcgguaucgcagCAGACGACUCGCUGAGGAUCCGAGA 3'

Clone deoxy 22 (SEQ ID NO: 14)
5' GGGAGGACGAUGCGGgaguagggagguaaucgucaccccaacgcggagacagcgaCAGACGACUCGCUGAGGAUCCGAGA 3'

Clone deoxy 24 (SEQ ID NO: 15)
5' GGGAGGACGAUGCGGaagcauacaguuuagugugcuagggugggacucagugauCAGACGACUCGCUGAGGAUCCGAGA 3'

Clone deoxy 28-A (SEQ ID NO: 16)
5' GGGAGGACGAUGCGGuccuacuuucccaauuuguaacagcucuccgcacagcagCAGACGACUCGCUGAGGAUCCGAGA 3'

Clone deoxy 30 (SEQ ID NO: 17)
5' GGGAGGACGAUGCGGcgguguagggaucgucagucucggaaugaccucacagaagCAGACGACUCGCUGAGGAUCCGAGA 3'

Clone deoxy 31 (SEQ ID NO: 18)
5' GGGAGGACGAUGCGGccagcaggaggaugggugccgcacucggauauucacguguCAGACGACUCGCUGAGGAUCCGAGA 3'

Clone deoxy 33-A (SEQ ID NO: 19)
5' GGGAGGACGAUGCGGgacuaagcacaacucaacuagaacgaaccuauuccaucauCAGACGACUCGCUGAGGAUCCGAGA 3'

Clone deoxy 34-D (SEQ ID NO: 20)
5' GGGAGGACGAUGCGGaacggaggagugccucucagcugacagucgugcauacuaCAGACGACUCGCUGAGGAUCCGAGA 3'

Clone deoxy 37-A (SEQ ID NO: 21)
5' GGGAGGACGAUGCGGaacucgauccaucaucgugacugcguacgugucaacuaagCAGACGACUCGCUGAGGAUCCGAGA 3'

Clone deoxy 40 (SEQ ID NO: 22)
5' GGGAGGACGAUGCGGgacggucauagagccggccgacauuagagccgggaauccaCAGACGACUCGCUGAGGAUCCGAGA 3'

Clone deoxy 44-A (SEQ ID NO: 23)
5' GGGAGGACGAUGCGGuggagaggggaaucguccugcgcacucugucuccugagagCAGACGACUCGCUGAGGAUCCGAGA 3'

Clone deoxy 45 (SEQ ID NO: 24)
5' GGGAGGACGAUGCGGuguauccgccaguaugauuaacaucuauaaguccuauguCAGACGACUCGCUGAGGAUCCGAGA 3'

Clone deoxy 46 (SEQ ID NO: 25)
5' GGGAGGACGAUGCGGcuaaccuuguuagggccccauacagcaucgagugacggauCAGACGACUCGCUGAGGAUCCGAGA 3'

Clone deoxy 47 (SEQ ID NO: 26)
5' GGGAGGACGAUGCGGugcacaggaggguguacacugcgcucgauucaucagcgcaCAGACGACUCGCUGAGGAUCCGAGA 3'

Clone deoxy 48 (SEQ ID NO: 27)
5' GGGAGGACGAUGCGGcaugugagggaggaggucccgcgucauaaacuccaggaccaCAGACGACUCGCUGAGGAUCCGAGA 3'

Clone deoxy 50 (SEQ ID NO: 28)
5' GGGAGGACGAUGCGGaagcaauagcucgccguacaguuguccugccguucguguuCAGACGACUCGCUGAGGAUCCGAGA 3'

Clone deoxy 52 (SEQ ID NO: 29)
5' GGGAGGACGAUGCGGgaguagggagguaagcagcggacuaacgagauucggugagCAGACGACUCGCUGAGGAUCCGAGA 3'

Clone EMdeoxy 8 (SEQ ID NO: 30)
5' GGGAGGACGAUGCGGcgagcaaccggaacucggcuauuaugaccagccaacuuaaCAGACGACUCGCUGAGGAUCCGAGA 3'
```

TABLE 1-continued

Complete Aptamer Sequences
(unique or representative of an identical family)

Clone EMdeoxy 8-A (SEQ ID NO: 31)
5' GGGAGGACGAUGCGGcgagcaaccugaacucggcuauuaggaccagccaacuuaaCAGACGACUCGCUGAGGAUCCGAGA 3'

Clone EMdeoxy 11 (SEQ ID NO: 32)
5' GGGAGGACGAUGCGGgaucggaaccagcgugacgaagcgcggaucaacuccggugCAGACGACUCGCUGAGGAUCCGAGA 3'

Clone EMdeoxy 11-A (SEQ ID NO: 33)
5' GGGAGGACGAUGCGGgaucggaaccagcgugacgaagcgcggaucaacuccggugCUGACGACUCGCUGAGGAUCCGAGA 3'

Clone EMdeoxy 12 (SEQ ID NO: 34)
5' GGGAGGACGAUGCGGccgauuagaacugggucgcgcuguacccuagggaucgaCAGACGACUCGCUGAGGAUCCGAGA 3'

OxyHbS Aptamer Sequences

Clone oxy 1 (SEQ ID NO: 35)
5' GGGAGGACGAUGCGGagacccaagcgccacgucuggcaugugagggaggagguacCAGACGACUCGCUGAGGAUCCGAGA 3'

Clone oxy 2 (SEQ ID NO: 36)
5' GGGAGGACGAUGCGGagagccaagcgccacgucuggcaugugagggggagguacCAGACGACUCGCUGAGGAUCCGAGA 3'

Clone oxy 3-B (SEQ ID NO: 37)
5' GGGAGGACGAUGCGGaaacucaucgguagccuuccugcggucagucuauuaggacCAGACGACUCGCUGAGGAUCCGAGA 3'

Clone oxy 4-B (SEQ ID NO: 38)
5' GGGAGGACGAUGCGGcaauuaccucagccucccuagacacgucgucuauuaggacCAGACGACUCGCUGAGGAUCCGAGA 3'

Clone oxy 5-A (SEQ ID NO: 39)
5' GGGAGGACGAUGCGGcagucuuccgguaagcacggaggugaggggagcuuagcguCAGACGACUCGCUGAGGAUCCGAGA 3'

Clone oxy 6 (SEQ ID NO: 40)
5' GGGAGGACGAUGCGGauaugccaugggucgcucgagugaggucgucuauuaggacCAGACGACUCGCUGAGGAUCCGAGA 3'

Clone oxy 7 (SEQ ID NO: 41)
5' GGGAGGACGAUGCGGagagccaagcgccacgucuggcaugugagggaggagguacCAGACGACUCGCUGAGGAUCCGAGA 3'

Clone oxy 8 (SEQ ID NO: 42)
5' GGGAGGACGAUGCGGauuggcgcuauuaggaccagcuccguccgcaacugguccGAGACGACUCGCUGAGGAUCCGAGA 3'

Clone oxy 9 (SEQ ID NO: 43)
5' GGGAGGACGAUGCGGgaacagacccauggcaaucucgcgacgucuucggccgcugCAGACGACUCGCUGAGGAUCCGAGA 3'

Clone oxy 10 (SEQ ID NO: 44)
5' GGGAGGACGAUGCGGuacaacagguucauacggcgcguuguuccuuggcugacgCAGACGACUCGCUGAGGAUCCGAGA 3'

Clone oxy 11 (SEQ ID NO: 45)
5' GGGAGGACGAUGCGGcacuauuaggaccagugccuguugucucgauaagcuccgcCAGACGACUCGCUGAGGAUCCGAGA 3'

Clone oxy 12 (SEQ ID NO: 46)
5' GGGAGGACGAUGCGGauuggcgcuauuaggaccagcuccguccgcaacugaucccGAGACGACUCGCUGAGGAUCCGAGA 3'

Clone oxy 13-A (SEQ ID NO: 47)
5' GGGAGGACGAUGCGGcuauuaggaccagccguguagaauucguagcgaugugacgCAGACGACUCGCUGAGGAUCCGAGA 3'

Clone oxy 13-B (SEQ ID NO: 48)
5' GGGAGGACGAUGCGGuucgcgcuauuaggaccagugcgaacgugggauacauguCAGACGACUCGCUGAGGAUCCGAGA 3'

Clone EMoxy 2-B (SEQ ID NO: 49)
5' GGGAGGACGAUGCGGaacacacgggacgagccuggcgguugucgucuauuaggacCAGACGACUCGCUGAGGAUCCGAGA 3'

Clone EMoxy 3 (SEQ ID NO: 50)
5' GGGAGGACGAUGCGGguccaugcuuuaaacugcaauuucccguuuacacgggcuguCAGACGACUCGCUGAGGAUCCGAGA 3'

Clone EMoxy 3-M (SEQ ID NO: 51)
5' GGGAGGACGAUGCGGaccaccgaaucacgaggugcgagacauugguuccccgccgCAGACGACUCGCUGAGGAUCCGAGA 3'

Clone EMoxy 4 (SEQ ID NO: 52)
5' GGGAGGACGAUGCGGgggacaauaguccacgacuacaugucggugcgucggagguCAGACGACUCGCUGAGGAUCCGAGA 3'

Clone EMoxy 6-A (SEQ ID NO: 53)
5' GGGAGGACGAUGCGGcuauuaggaccagcugccaauguuaagucuaccccagcagCAGACGACUCGCUGAGGAUCCGAGA 3'

Clone EMoxy 6-C (SEQ ID NO: 54)
5' GGGAGGACGAUGCGGcuuacguauggucacggaggugugggggaacauacagcagCAGACGACUCGCUGAGGAUCCGAGA 3'

Clone EMoxy 8 (SEQ ID NO: 55)
5' GGGAGGACGAUGCGGuuggugaccuauucaggcguaggcauauaaacuacgaggcCAGACGACUCGCUGAGGAUCCGAGA 3'

TABLE 1-continued

Complete Aptamer Sequences
(unique or representative of an identical family)

Clone EMoxy 9 (SEQ ID NO: 56)
5' GGGAGGACGAUGCGGcuauuaggaccagcugccaauguuaagucuacccagcggCAGACGACUCGCUGAGGAUCCGAGA 3'

Clone EMoxy 11 (SEQ ID NO: 57)
5' GGGAGGACGAUGCGGgcacgacacgccgauuagaacugggcgaucuuggucgagcCAGACGACUCGCUGAGGAUCCGAGA 3'

Clone EMoxy 12 (SEQ ID NO: 58)
5' GGGAGGACGAUGCGGcgauacgaccgcaugaguauaccgucgugcuucccggcugCAGACGACUCGCUGAGGAUCCGAGA 3'

Clone EMoxy 13 (SEQ ID NO: 59)
5' GGGAGGACGAUGCGGauuggcgcuauuaggaccagcuccguccgcaaccgguccCAGACGACUCGCUGAGGAUCCGAGA 3'

Clone EMoxy 14 (SEQ ID NO: 60)
5' GGGAGGACGAUGCGGauuggcgcuauuaggaccagcuccguccgcaacugguccCAGACGACUCGCUGAGGAUCCGAGA 3'

Aptamer Pools Generated that Bind Specifically to Deoxy-HbS

Binding of the deoxy HbS-selected aptamers to oxy- and deoxy-hemoglobin was assessed at various rounds of selection. FIG. 1 shows that by the end of the selection process, the aptamers selected against deoxy hemoglobin bind to deoxy hemoglobin in a dose dependent saturable manner.

Aptamer Deoxy-3-A Inhibits Polymerization of Deoxygenated HbS

In order to evaluate individual aptamers' ability to inhibit polymerization, aptamers were amplified and added to an anaerobic solution of deoxygenated HbS, in which spectrophotometric measurements of turbidity at a wavelength of 700 nm reflected the extent of polymerization. It was necessary to develop a system in which HbS would reliably and reproducibly polymerize using the smallest possible concentration in order to minimize the quantities of aptamer necessary for testing. In HbS polymerization studies, shorter lag times and higher polymerization rates are associated with higher temperature, higher hemoglobin concentration, the use of potassium phosphate buffer, and higher buffer concentrations; therefore, in order to enhance polymerization in a low concentration HbS system, we utilized a buffer solution of 1.49 M potassium phosphate buffer and conducted the incubations at 37° C. Sodium dithionite at a concentration of 0.48 mM was used to deoxygenate HbS. Test assays (data not shown) showed that this concentration of sodium dithionite in our system consistently resulted in solutions of 93-96% deoxygenated HbS.

Each aptamer was tested at a concentration of 0.01 mM (an aptamer to heme molar ratio of 1:12). From the initial set of activity assays, an aptamer denoted deoxy-3-A (SEQ ID NO:4) was identified as causing reduced polymerization, with increased lag times and decreased maximal polymerization over the time frame of the experiment (FIG. 2). This is proof of principle that an RNA aptamer can alter the polymerization of HbS, and shows that this agent could be useful as a therapy for sickle cell anemia. It also describes a specific, unique, but modifiable aptamer reagent that has this property. FIG. 2 summarizes data for 4 separate experiments with the deoxy 3-A aptamer (SEQ ID NO:4), demonstrating consistent inhibition of HbS polymerization in multiple runs as compared to a control aptamer (SM20) or water control. Preliminary results from two additional aptamers, Deoxy-1 (SEQ ID NO:2) and Deoxy EM8-A (SEQ ID NO:31), have shown some inhibition of polymerization as well (FIGS. 3 and 4). FIG. 5 summarizes data for the Oxy 3-B aptamer (SEQ ID NO:37), demonstrating consistent inhibition of HbS polymerization in multiple runs as compared to water control.

To determine if deoxy 3-A inhibited polymerization of HbS in a dose-dependent manner, HbS polymerization studies were performed as previously described in the presence of increasing concentrations of the deoxy-3A aptamer from 0.3125 micromolar to 10 micromolar final concentration. Water only controls as well as non-specific aptamer controls were performed. FIG. 6A shows a clear concentration-dependent inhibition of polymerization by the deoxy-3A aptamer. Additionally, the dose response was quantified by determining the slope of the polymerization curves as a function of deoxy 3-A aptamer concentration (FIG. 6B). The slopes, as measured from time points 22-50 minutes in the dose response curves, were calculated and plotted as a function of aptamer concentration to display the dose-dependent effects of this aptamer in inhibiting polymerization.

Lipofectin Facilitates Entry of Deoxy 3-A Aptamer into Sickle Red Blood Cells

To determine if lipofectin could facilitate entry of the deoxy 3-A aptamer into sickle red blood cells, sickle red blood cells obtained with consent from patients were washed and subjected to transfection using a standard protocol with Lipofectin reagent in the presence or absence of fluorescently labeled deoxy 3-A aptamer. The cells were vigorously washed in high salt buffer following transfection to remove any non-specifically bound aptamer. Increased fluorescence intensity of the population demonstrates successful transfer of deoxy 3-A into red blood cells. Fluorescent microscopy following transfection confirmed the introduction of the deoxy 3-A aptamer into a subset of the red blood cells (FIG. 7).

HbS Retains the Ability to Form New Polymer when Growing Filament Ends are Provided by Mechanical Disruption To evaluate the ability of HbS to form new polymer when growing filament ends were provided by mechanical disruption, polymerization assays were performed as previously described. At the end of the assay, cuvettes containing HbS or HbS plus aptamer were shaken in an effort to break long filaments and supply new ends for a polymerization reaction. HbS in the presence of the deoxy 3-A aptamer was capable of forming new polymer, demonstrating that the aptamer is not merely causing protein denaturation over time as a mechanism of action (FIG. 8).

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A RNA aptamer comprising a nucleotide sequence selected from the group consisting of the nucleotide sequence of any one of SEQ ID NOS: 2-34.

2. The RNA aptamer of claim 1 comprising a nucleotide sequence selected from the group consisting of the nucleotide sequence of any one of SEQ ID NOS: 2, 4, 31, and 34.

3. The RNA aptamer of claim 1, wherein the polynucleotide aptamer is modified to increase its circulating half-life after administration to a subject.

4. A polynucleotide encoding the RNA aptamer of claim 3.

5. A vector comprising the polynucleotide of claim 4.

6. A cell comprising the RNA aptamer of claim 1.

7. A method of treating sickle cell disease in a subject in need thereof, the method comprising administering to the subject a therapeutically effective amount of a RNA aptamer that specifically binds deoxygenated HbS (deoxy-HbS), wherein the RNA aptamer inhibits polymerization of deoxy-HbS, and wherein the RNA aptamer comprises a nucleotide sequence selected from the group consisting of the nucleotide sequence of any one of SEQ ID NOS: 2, 4,and 31.

8. The method of claim 7, wherein the RNA aptamer is modified to increase its circulating half-life after administration to the subject.

9. The method of claim 8, wherein the RNA aptamer is in a pharmaceutically acceptable carrier.

10. The method of claim 7, wherein the sickle cell disease is sickle cell anemia.

* * * * *